(12) United States Patent
Chung et al.

(10) Patent No.: US 9,371,350 B2
(45) Date of Patent: *Jun. 21, 2016

(54) TREHALOSE DERIVATIVES AND PHARMACEUTICAL COMPOSITIONS FOR TREATING NEURODEGENERATIVE DISEASES

(71) Applicant: POSTECH ACADEMY-INDUSTRY FOUNDATION, Pohang-shi, Gyeongsangbuk-do (KR)

(72) Inventors: Sung-Kee Chung, Pohang-si (KR); Woo Sirl Lee, Guri-si (KR); Boram Kim, Gwangju-si (KR); Jungkyun Im, Seoul (KR); Subhash C. Ghosh, Pohang-si (KR)

(73) Assignee: POSTECH FOUNDATION, Pohang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/509,175

(22) Filed: Oct. 8, 2014

(65) Prior Publication Data

US 2015/0025035 A1 Jan. 22, 2015

Related U.S. Application Data

(62) Division of application No. 13/003,414, filed as application No. PCT/KR2009/001470 on Mar. 23, 2009, now abandoned.

(30) Foreign Application Priority Data

Jul. 22, 2008 (KR) ........................ 10-2008-0071383

(51) Int. Cl.
*C07H 15/04* (2006.01)
*C07H 3/04* (2006.01)

(52) U.S. Cl.
CPC . *C07H 3/04* (2013.01); *C07H 15/04* (2013.01)

(58) Field of Classification Search
CPC ....................................................... C07H 15/04
See application file for complete search history.

(56) References Cited

U.S. PATENT DOCUMENTS

2007/0111970 A1    5/2007   Cruz et al.

FOREIGN PATENT DOCUMENTS

| JP | 2007-523889 A | 8/2007 |
| JP | 2008-063316 A | 3/2008 |
| JP | 2008-539226 A | 11/2008 |
| WO | 2004/075882 A1 | 9/2004 |
| WO | 2006/115312 A1 | 11/2006 |

OTHER PUBLICATIONS

Ross et al., Nature Medicine, 2004, 10, p. S10-S17.*
Miura et al., Sci. Technol. Adv. Mater., 2008, (2)9, p. 1-6.*
Wang et al., PNAS, 2009, 106(5), p. 1392-1397.*
Japanese Patent Office, Japanese Office Action issued in corresponding JP Application No. 2011-519969, dated May 14, 2013.
McLaurin et al., J. Biol. Chem., 2000, 275(24), p. 18495-18502.
McLaurin e tal., Nature Medicine, 26, 12(7), p. 801-808.
Salloway et al., Neurology, 2011, 77, p. 1253-1262.
Liu et al., Neurobiology of Disease, Blackwell Scientific Publications, Oxford, GB, 20(1): 74-81 (2005).
Motomasa Tanaka et al, Nature Medicine, 10(2):148-154 (2004).
European Patent Office, communication dated Jan. 20, 2016 in counterpart application No. 15186646.4.

* cited by examiner

*Primary Examiner* — Jonathan S Lau
(74) *Attorney, Agent, or Firm* — Sughrue Mion, PLLC

(57) ABSTRACT

The invented inositol and trehalose derivatives, prepared by introducing multiple units of the guanidine group to the backbone molecules, show excellent blood-brain barrier permeability, and accordingly, it can be easily transported to the brain tissues and utilized for the treatment of neurodegenerative diseases such as Alzheimer's disease and Huntington's disease.

3 Claims, 1 Drawing Sheet

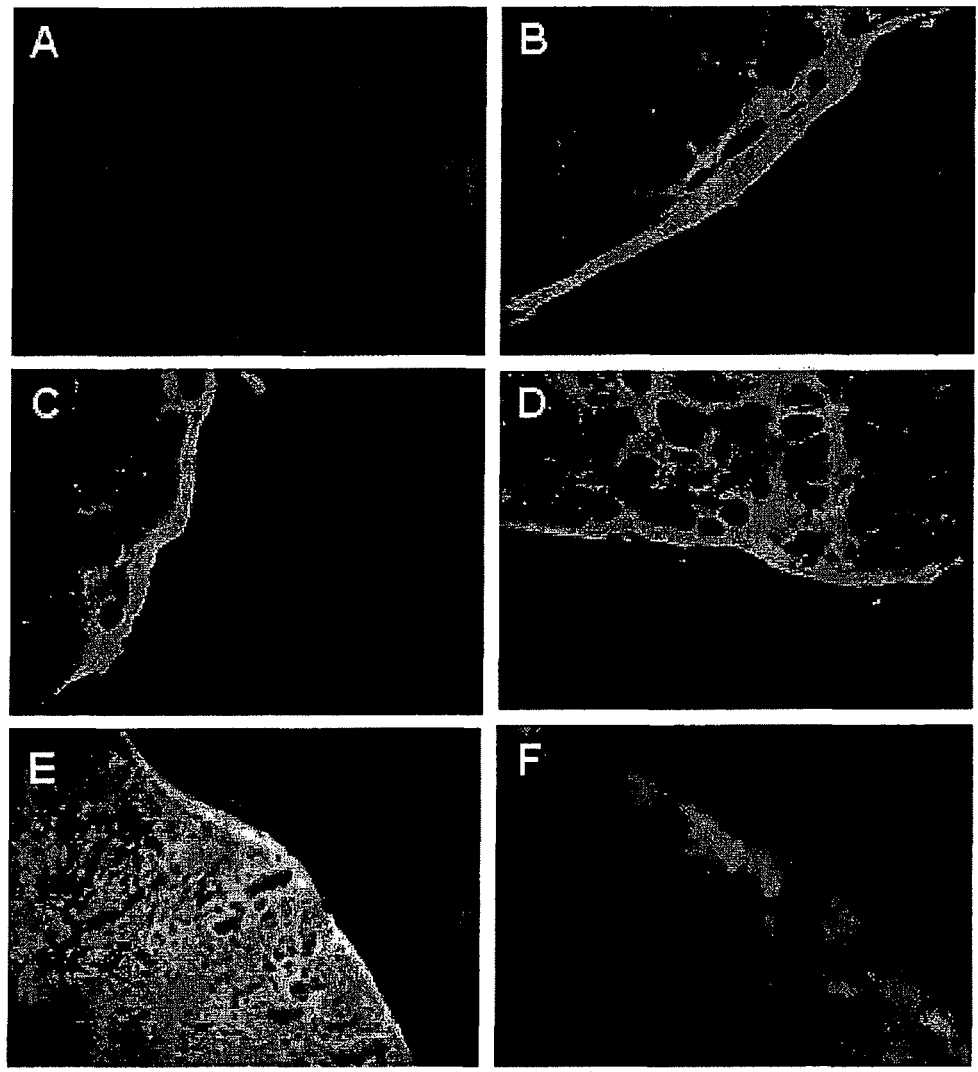

TREHALOSE DERIVATIVES AND PHARMACEUTICAL COMPOSITIONS FOR TREATING NEURODEGENERATIVE DISEASES

CROSS-REFERENCE TO RELATED APPLICATIONS

This application is a divisional of U.S. patent application Ser. No. 13/003,414, filed Jan. 10, 2011, which is a national stage application of PCT/KR2009/001470 filed Mar. 23, 2009, which claims priority from Korean Patent Application No. 10-2008-0071383 filed Jul. 22, 2008, the disclosure of which is incorporated herein by reference in its entirety.

FIELD OF THE INVENTION

The present invention relates to inositol and trehalose derivatives having excellent blood-brain barrier permeability, which are prepared by introducing several guanidine groups to the backbone of inositol and trehalose, and to pharmaceutical compositions for treating neurodegenerative diseases comprising the same.

BACKGROUND OF THE INVENTION

Approximately 25 million people worldwide are currently suffering from Alzheimer's disease, and that number is expected to double every five years. Studies of the brain tissue of Alzheimer's disease patients have revealed the presence of aggregated peptides, particularly senile plaques and neurofibrillary tangles, which have been reported to be formed from mutated beta-amyloids and Tau peptides (M. Goedert, M. G. Spillantini, *Science*, 314: 777-784 (2006)). Such aggregated peptides induce cell damage and apoptosis, resulting in neurodegenerative diseases. The presently available methods of symptomatic therapy include the use of acetylcholinesterase inhibitors and NMDA acceptor antagonists, but such agents do not cure the disease.

It has been reported that some inositol stereoisomers prevent beta-amyloids from forming aggregates in in vitro experiments, and also that they are capable of inhibiting the aggregation of beta-amyloids in mouse models of Alzheimer's disease to reduce or alleviate the symptoms of Alzheimer's disease (J. McLaurin et al., *Nature Medicine*, 12: 801-808 (2006); J. McLaurin et al., *J. Biol. Chem.* 275: 18495-18502 (2000). However, inositol is known to have difficulty in passing through the blood-brain barrier (BBB), and the amount thereof transferred to the nervous system of the brain is insignificantly small (L. M. Lewin et al., *Biochem. Journal*, 156: 375-380 (1976); M. Uldry et al., *EMBO Journal*, 20: 4467-4477 (2000). Hence, in order to apply inositol to the treatment of Alzheimer's disease, a method to enhance the passage of inositol through the BBB must be developed.

Huntington's disease, a neurodegenerative disease inducing dementia, afflicts approximately 30,000 Americans. It has been shown that most Huntington's disease patients have a mutation in the CAG (glutamine codon) repeats of chromosome No. 4, which leads to the production of mutant huntingtin proteins (H. Y. Zoghbi, H. T. Orr, *Annu. Rev. Neuroscie.*, 23: 217-247 (2000). The mutant huntingtin proteins are reported to induce mitochondrial dysfunction in specific nerve cells of the brain, causing the apoptosis of the nerve cells. No therapeutically effective agent for Huntington's disease has been developed.

Trehalose has been reported to efficiently inhibit the polyglutamine-induced aggregate formation in in vivo mouse model experiments, alleviating the symptoms of Huntington's disease (M. Tanaka et al., *Nature Medicine*, 10: 148-154 (2004). However, it is also known that trehalose cannot pass through the BBB to reach the brain (www.huntingtonproject.org/portals/0/trehalose). Thus, in order to use trehalose as an effective therapeutic agent for Huntington's disease, a method that enables trehalose to pass through the BBB must be developed.

Therefore, the present inventors have endeavored to develop inositol and trehalose derivatives that can pass through the BBB and reach the brain for effective treatment of Alzheimer's disease and Huntington's disease, respectively.

SUMMARY OF THE INVENTION

Accordingly, it is the object of the present invention to provide inositol derivatives, trehalose derivatives, and monosaccharide derivatives, which have improved BBB permeability.

It is another object of the present invention to provide pharmaceutical compositions for the treatment of neurodegenerative diseases, comprising the inositol derivatives, the trehalose derivatives, and the monosaccharide derivatives.

In accordance with one aspect of the present invention, are provided inositol derivatives of Formula (1) or salts thereof:

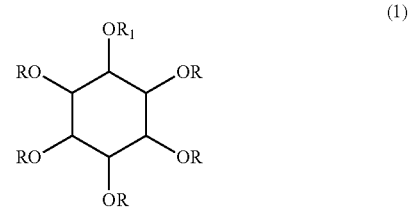

(1)

wherein,
R is

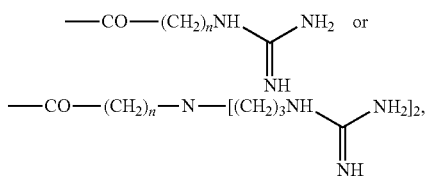

n being an integer in the range of 1 to 12; and
$R_1$ is hydrogen, R, alkyl or —COR', R' being hydrogen, alkyl, aminoalkyl, arylalkyl, cycloalkyl or heteroalkyl.

In accordance with another aspect of the present invention, are provided inositol derivatives of Formula (2) or salts thereof:

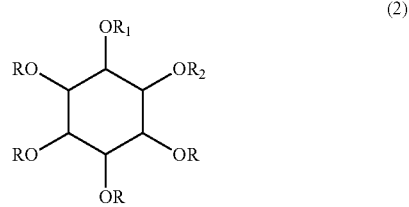

(2)

wherein,
R is $$-CO-(CH_2)_n-N-[(CH_2)_3NH-C(=NH)-NH_2]_2,$$

n being an integer in the range of 1 to 12; and
$R_1$ and $R_2$ are each independently hydrogen, alkyl or —COR', R' being hydrogen, alkyl, aminoalkyl, arylalkyl, cycloalkyl or heteroalkyl.

In accordance with a further aspect of the present invention, are provided trehalose derivatives of Formula (3) or salts thereof:

$$(3)$$

wherein,
R is n $$-CO-(CH_2)_nNH-C(=NH)-NH_2,$$

being an integer in the range of 1 to 12; and
$R_1$ is hydrogen, R, alkyl or —COR', R' being hydrogen, alkyl, aminoalkyl, arylalkyl, cycloalkyl, heteroalkyl or a phosphor.

In accordance with a further aspect of the present invention, are provided monosaccharide derivatives of Formula (4) or salts thereof:

$$(4)$$

wherein,
R is $$-CO-(CH_2)_nNH-C(=NH)-NH_2 \text{ or}$$
$$-CO-(CH_2)_n-N-[(CH_2)_3NH-C(=NH)-NH_2]_2,$$

n being an integer in the range of 1 to 12;
$R_1$ is hydrogen, R, alkyl, arylalkyl, cycloalkyl or heteroalkyl; and
$R_2$ is hydrogen, R or trityl.

In addition, in accordance with a still further aspect of the present invention, are provided pharmaceutical compositions for treating neurodegenerative diseases, comprising any one compound selected from the compounds of Formulas 1 to 4.

BRIEF DESCRIPTION OF THE DRAWINGS

The above and other objects and features of the present invention will become apparent from the following description of the invention, when taken in conjunction with the accompanying FIG. 1, which shows the abilities of the compounds according to the present invention to permeate into the brain through the BBB.

DETAILED DESCRIPTION OF THE INVENTION

Unless otherwise defined, the technical and scientific terms used in the present invention have the same meanings generally used in the relevant technical field. In addition, the aforementioned literatures are incorporated into the description of the invention by reference.

Herein, the term "alkyl" refers to a linear or branched $C_{1-12}$ alkyl, e.g., methyl, ethyl, propyl, hexyl, and octyl.

The term "aryl" refers to a monocyclic aromatic group or a bicyclic group having one or more aromatic rings, and the term "arylalkyl" refers to a $C_{1-3}$ alkyl having 1 to 3 aryl substituents, including but not limited to benzyl, and trityl.

The term "cycloalkyl" refers to a saturated monocyclic $C_{3-8}$ hydrocarbon group, including but not limited to cyclopropyl, cyclobutyl, and cyclohexyl.

Further, the term "heteroalkyl" refers to a $C_{1-10}$ alkyl having one or more heteroatoms, the heteroatom being oxygen, sulfur, or nitrogen.

Hereinafter, a detailed description of the present invention is given.

The present invention provides inositol derivatives of Formula (1) or salts thereof:

$$(1)$$

wherein,
R is $$-CO-(CH_2)_nNH-C(=NH)-NH_2 \text{ or}$$
$$-CO-(CH_2)_n-N-[(CH_2)_3NH-C(=NH)-NH_2]_2,$$

n being an integer in the range of 1 to 12; and
$R_1$ is hydrogen, R, alkyl or —COR', R' being hydrogen, alkyl, aminoalkyl, arylalkyl, cycloalkyl or heteroalkyl.

The stereochemistry of the compound of Formula (1) corresponds to the scyllo-, rnyo-, epi-, chiro-, allo-, muco-, neo- or cis-inositol isomer.

Also, the present invention provides inositol derivatives of Formula (2) or salts thereof:

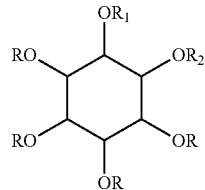 (2)

wherein,
R is

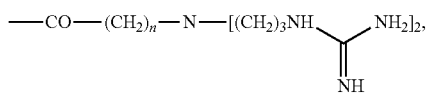

n being an integer in the range of 1 to 12; and $R_1$ and $R_2$ are each independently hydrogen, alkyl or —COR', R' being hydrogen, alkyl, aminoalkyl, arylalkyl, cycloalkyl or heteroalkyl.

The structural framework of the compound of Formula (2) corresponds to the scyllo-, rnyo-, epi-, or chiro-inositol isomer Also, the present invention provides trehalose derivatives of Formula (3) or salts thereof:

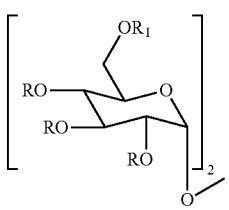 (3)

wherein,
R is

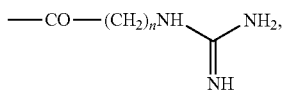

n being an integer in the range of 1 to 12; and $R_1$ is hydrogen, R, alkyl or —COR', R' being hydrogen, alkyl, aminoalkyl, arylalkyl, cycloalkyl, heteroalkyl or a fluorescence probe.

Also, the present invention provides a monosaccharide derivative of Formula (4) or a salt thereof:

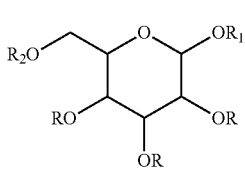 (4)

wherein,
R is

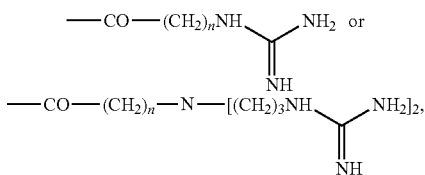

n being an integer in the range of 1 to 12;

$R_1$ is hydrogen, R, alkyl, arylalkyl, cycloalkyl or heteroalkyl; and $R_2$ is hydrogen, R or trityl.

The compound of Formula (4) has the structural framework of D-glucose, D-mannose, D-allose or D-galactose.

The inositol derivatives of Formulas (1) and (2) according to the present invention may be prepared by a method comprising the steps of: 1) introducing amino acid side chains to the hydroxyl groups of a protected inositol intermediate by acylation to obtain an intermediate; 2) introducing protected guanidine groups to the terminal amino groups of the amino acid side chains of the compound obtained in step 1); and 3) removing the protecting group from the guanidine group of the compound obtained in step 2) to provide the inositol derivative of Formulas (1) or (2).

The trehalose derivatives of Formula (3) according to the present invention may be prepared by a method comprising the steps of: 1) introducing amino acid side chains to the hydroxyl groups of a protected trehalose intermediate by acylation to obtain an intermediate; 2) introducing protected guanidine groups to the terminal amino groups of the amino acid side chains of the compound obtained in step 1); and 3) removing the protecting group from the guanidine group of the compound obtained in step 2) to provide the trehalose derivative of Formula (3).

The monosaccharide derivatives of Formula (4) according to the present invention may be prepared by a method comprising the steps of: 1) introducing amino acid side chains to the hydroxyl groups of a protected monosaccharide intermediate by acylation to obtain an intermediate; 2) introducing protected guanidine groups to the terminal amino groups of the amino acid side chains of the compound obtained in step 1); and 3) removing the protecting group from the guanidine group of the compound obtained in step 2) to provide the monosaccharide derivative of Formula (4).

Specifically, the intermediate for preparing the compound of Formula (1) can be prepared according to the procedure of Scheme (1) using a scyllo-inositol derivative, in which the stereochemistry of the 2-OH group of myo-inositol is inverted, as a starting material.

Scheme (1)

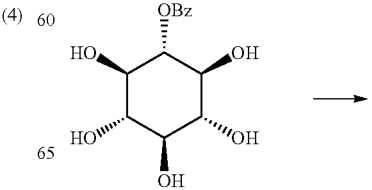

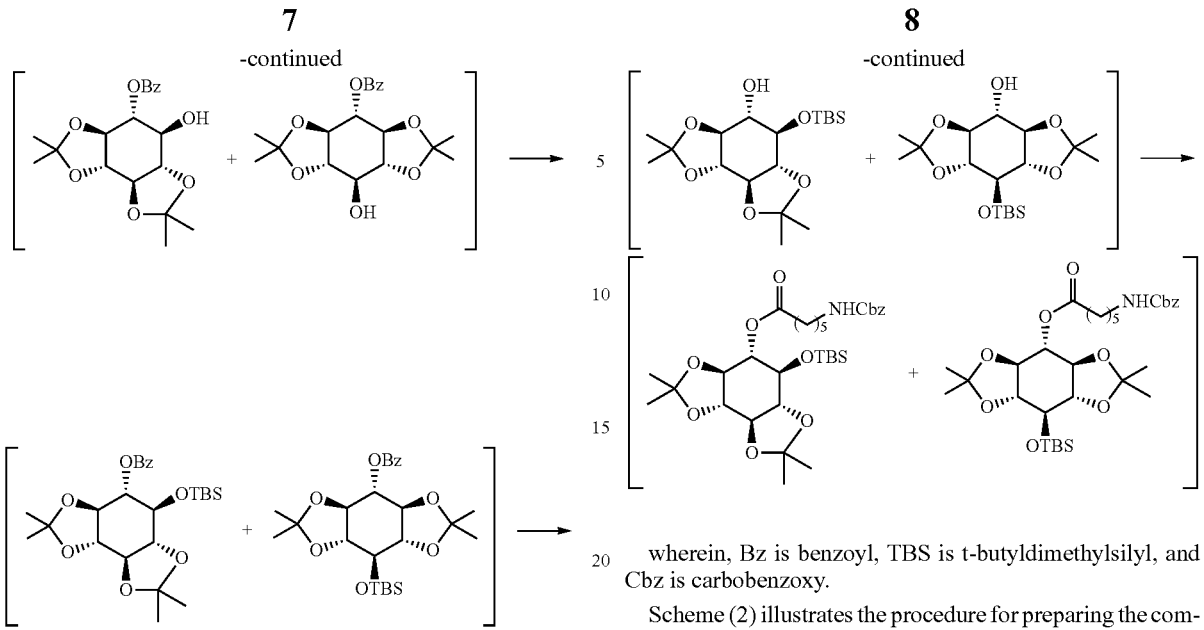
wherein, Bz is benzoyl, TBS is t-butyldimethylsilyl, and Cbz is carbobenzoxy.
Scheme (2) illustrates the procedure for preparing the compound of Formula (1) from the intermediate obtained in Scheme (1).
Scheme (2)
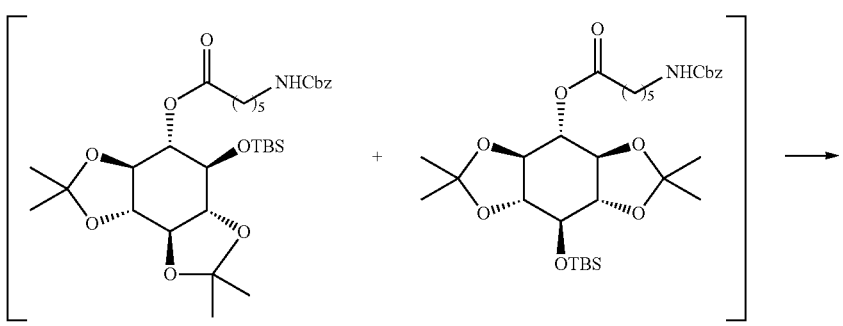
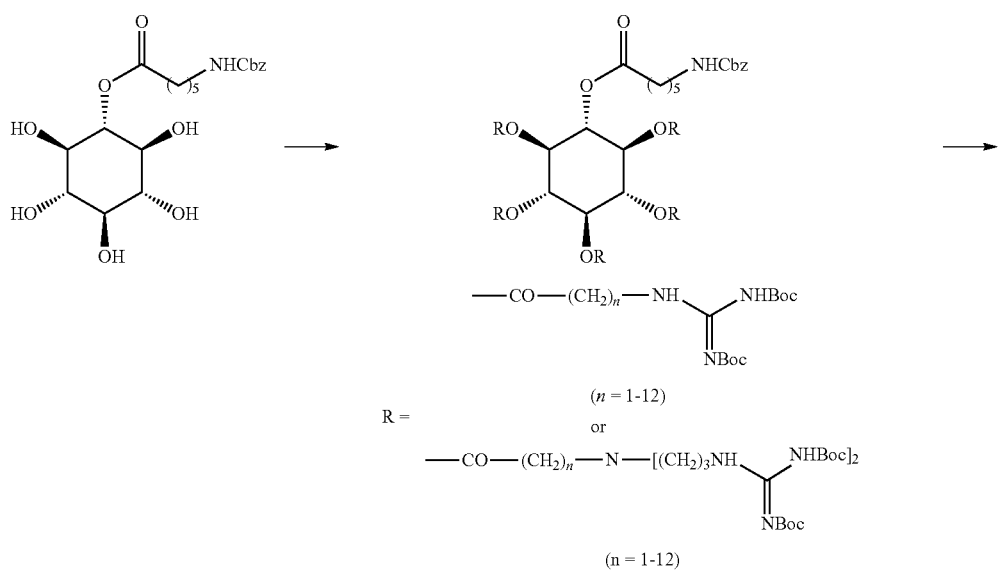

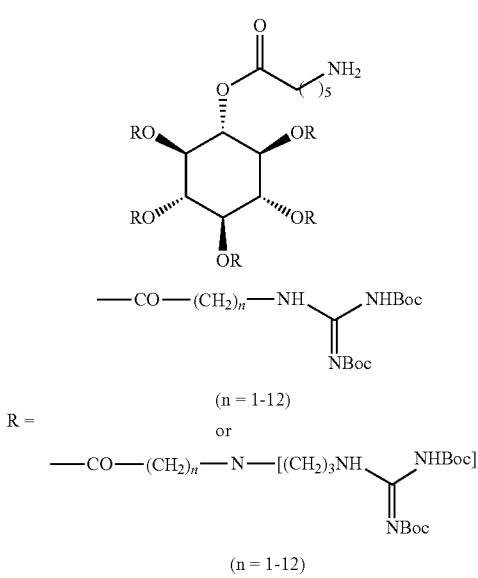
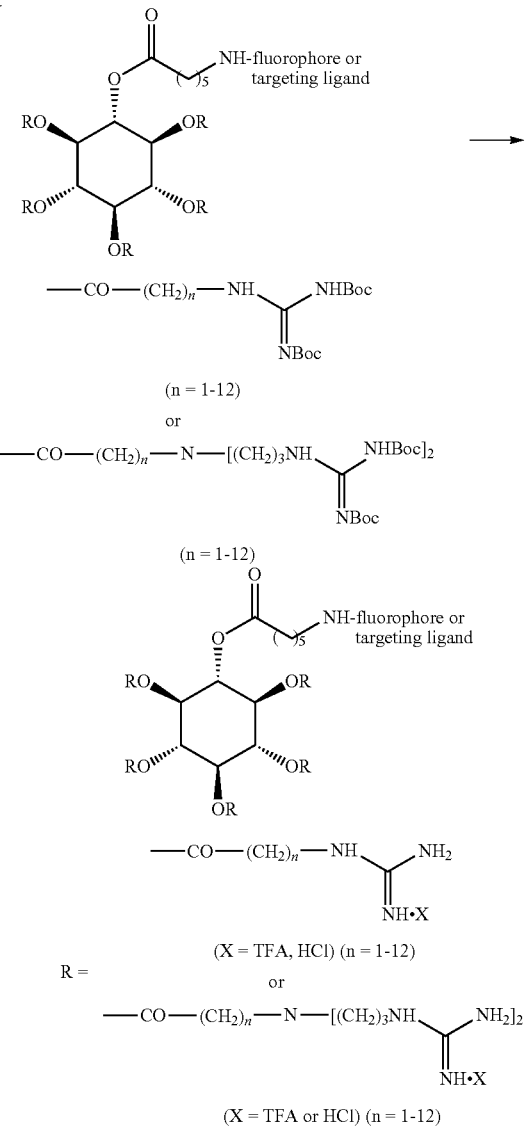
wherein, Boc is butyloxycarbonyl, TFA is trifluoroacetic acid, and Cbz and TBS are the same as defined above.
The compound of Formula (2) which is a typical example of the inositol derivative having eight guanidine groups, can be prepared from 1-O-benzoyl-2,3,4,5-tetrabenzyl-scyllo-inositol (Korean Patent No. 578732) according to the procedure of Scheme (3).
Scheme (3)
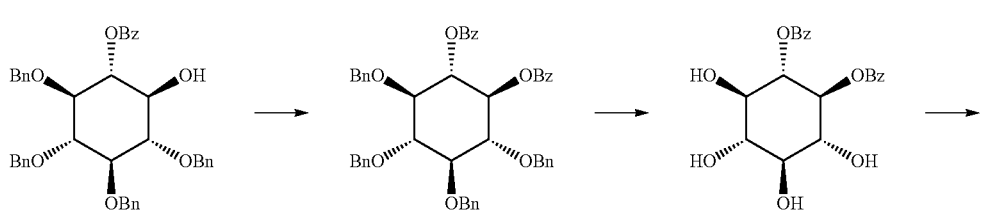
A

 
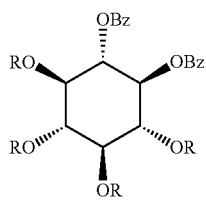 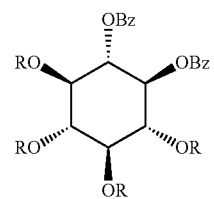
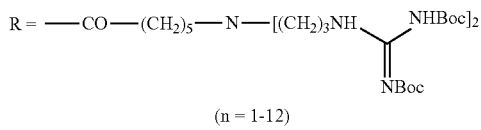 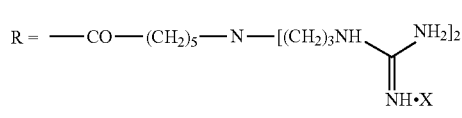
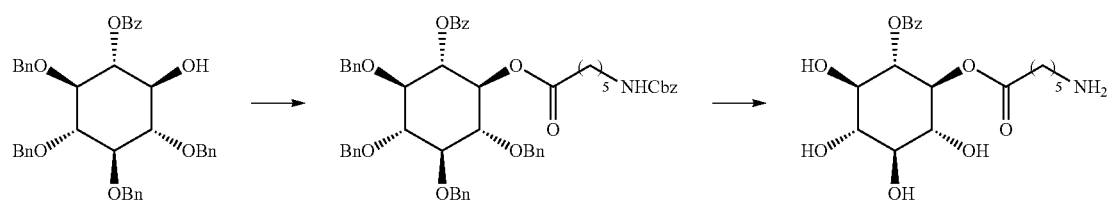
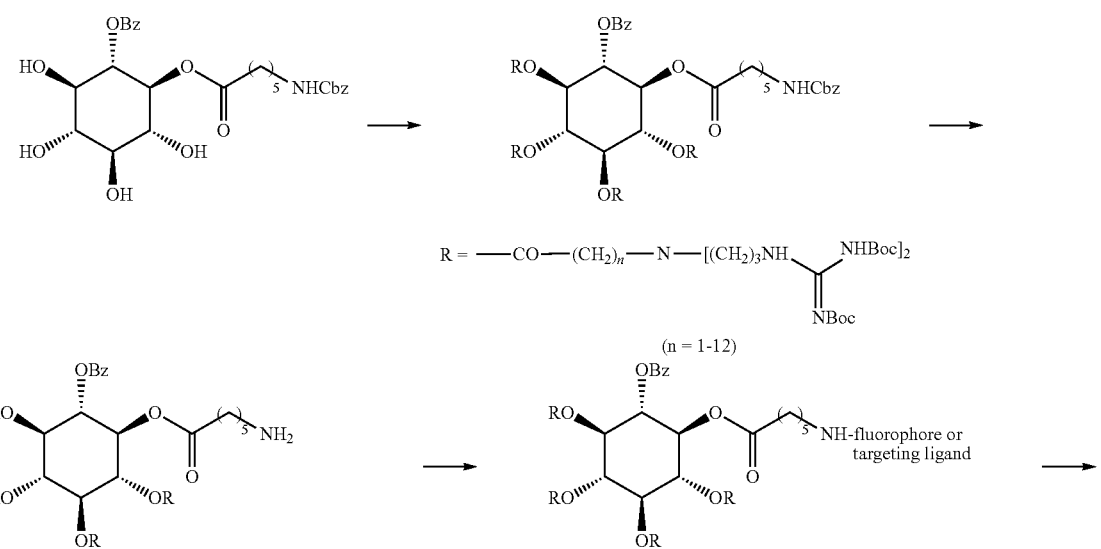
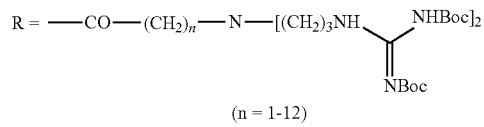 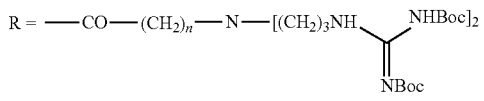
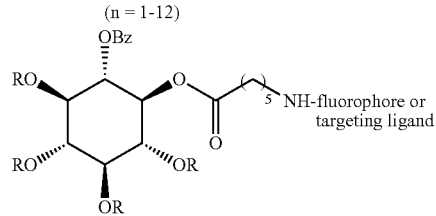
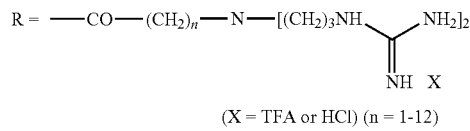

wherein, Bn is benzyl, and Bz, Boc, Cbz and TFA are the same as defined above.

Schemes (4) and (5) respectively illustrate the procedures for preparing the compounds of Formula (3) from trehalose.

wherein, Boc and TFA are the same as defined above.

Scheme (4)

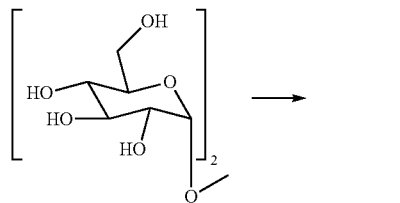

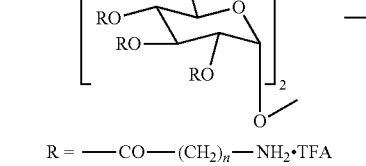

R = —CO—(CH$_2$)$_n$—NHBoc (n = 1-12)

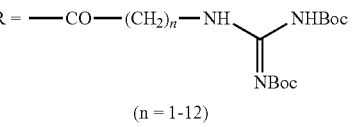

R = —CO—(CH$_2$)$_n$—NH$_2$·TFA (n = 1-12)

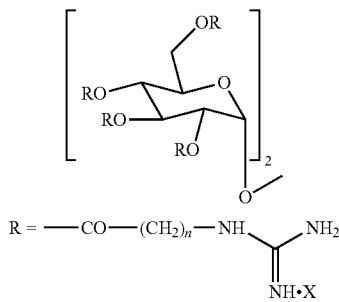

R = —CO—(CH$_2$)$_n$—NH

NHBoc

NBoc (n = 1-12)

R = —CO—(CH$_2$)$_n$—NH

NH$_2$

NH·X (X = TFA or HCl)

(n = 1-12)

Scheme (5)

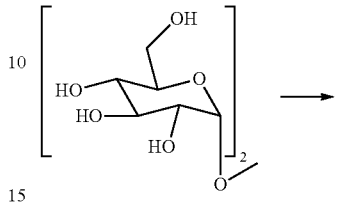

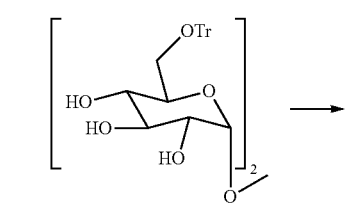

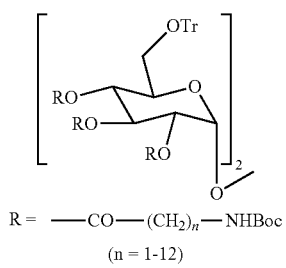

R = —CO—(CH$_2$)$_n$—NHBoc (n = 1-12)

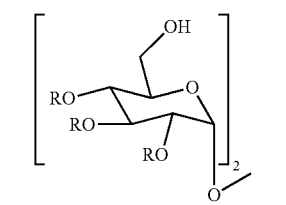

R = —CO—(CH$_2$)$_n$—NH$_2$·HCl (n = 1-12)

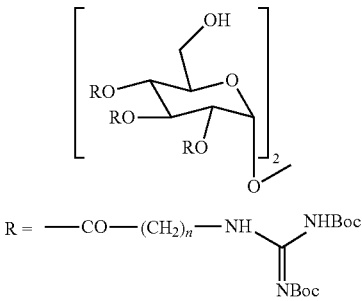

R = —CO—(CH$_2$)$_n$—NH

NHBoc

NBoc (n = 1-12)

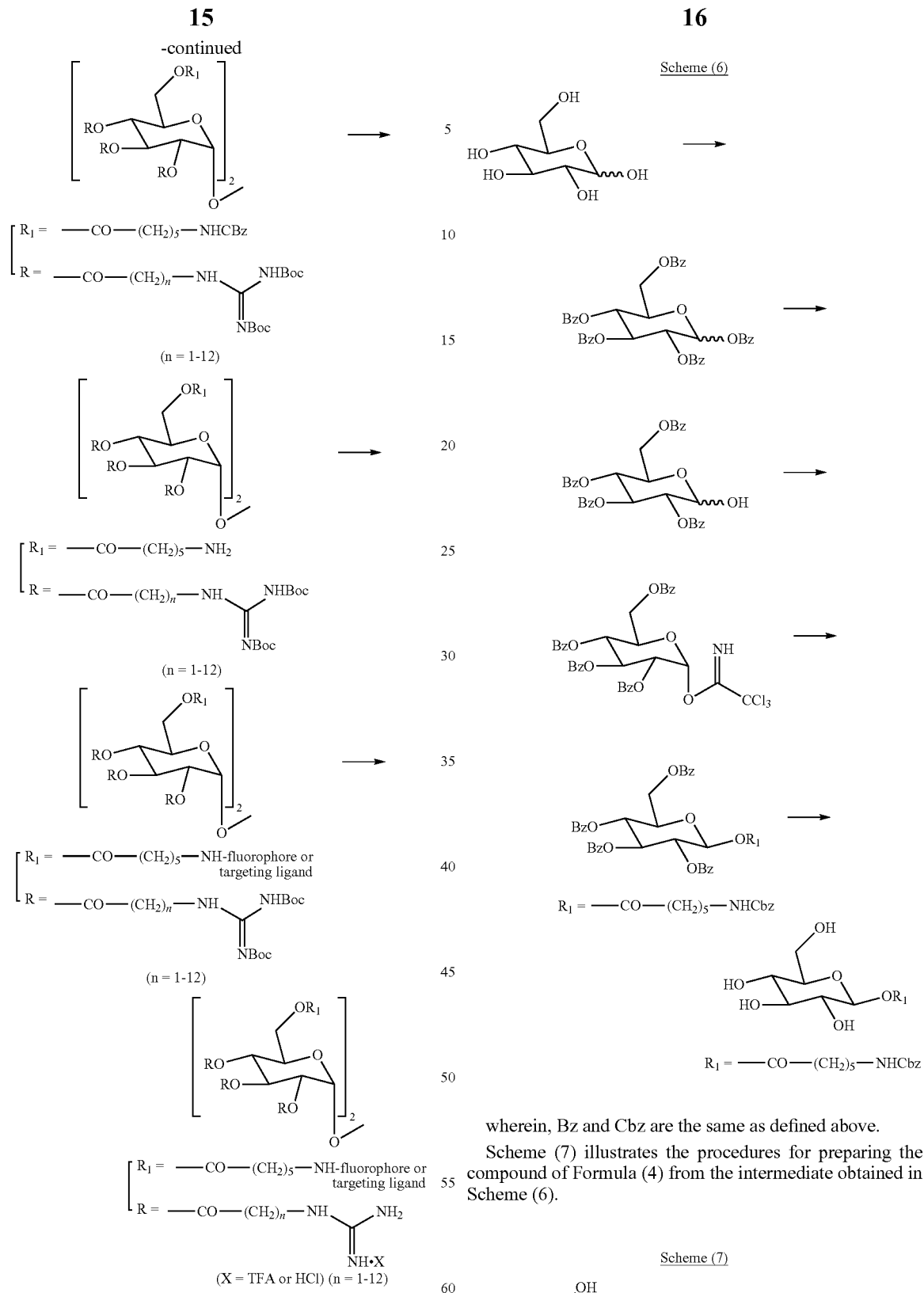

wherein, Tr is trityl, FITC is fluorescein isothiocyanate, and Boc, Cbz and TFA are the same as defined above.

The key intermediate for preparing the compound of Formula (4) can be prepared according to the procedure of Scheme (6) using D-glucose as a starting material.

wherein, Bz and Cbz are the same as defined above.

Scheme (7) illustrates the procedures for preparing the compound of Formula (4) from the intermediate obtained in Scheme (6).

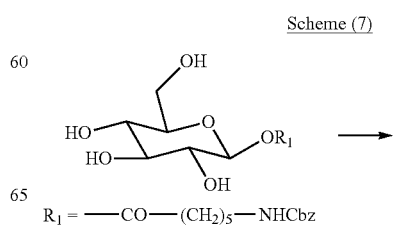

-continued

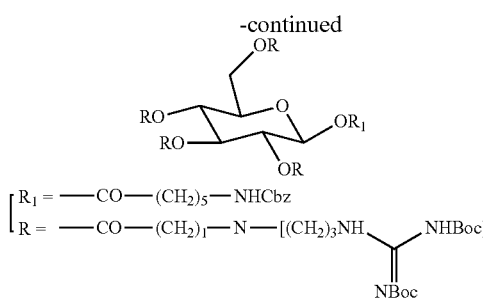

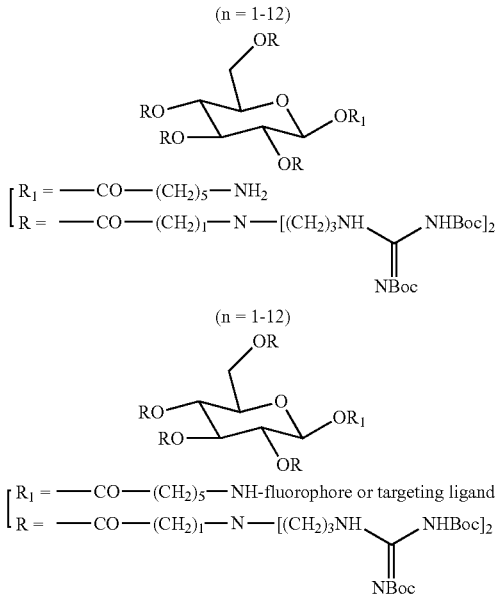

(X = TFA or HCl)
(n = 1-12)

wherein, Cbz, Boc and TFA are the same as defined above.

The present invention provides pharmaceutical compositions for treating neurodegenerative diseases, comprising any one compound selected from the compounds of Formulas 1 to 4 and a pharmaceutically acceptable carrier. The neurodegenerative diseases may include Alzheimer's disease, Huntington's disease, and closely related diseases.

The pharmaceutical composition according to the present invention may further include an excipient, a disintegrator, a sweetening agent, a lubricating agent, and a flavoring agent, which are typically used. Also, the pharmaceutical composition may be formulated into pharmaceutical preparations in single- or multiple-dose forms, such as tablets, capsules, powders, granules, liquids such as suspensions, emulsions or syrups, or parenteral administration preparations, by typical methods.

Also, the pharmaceutical composition according to the present invention may be parenterally or orally administered depending on the needs, and daily dose of the compound of the present invention may be 0.01 to 100 mg per 1 kg of adult's body weight and may be administered at once or in several parts. The dose for a specific patient may vary depending on body weight, age, gender, health condition, diet, administration time, administration method, and disease severity.

The following Examples are intended to further illustrate the present invention without limiting its scope.

EXAMPLE

Preparative Example 1

Preparation of Scyllo-Inositol Having Carbobenzoxy (Cbz)-Protected Linker

<1-1> Introduction of Acetonide Protecting Group

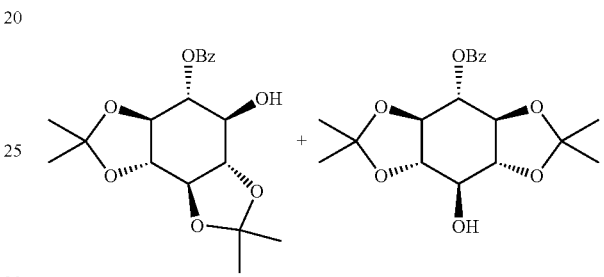

1-O-Bz-2,3,4,5,6-pentahydroxyl-scyllo-inositol (Korean Patent No. 578732; 9.96 g, 35.05 mmol) was dissolved in N,N-dimethylformamide (110 ml), and para-toluene sulfonic acid (3.33 g) was added dropwise thereto to obtain a mixture. 2-Methoxypropene (33.5 ml) was added to the mixture and the mixture was stirred at room temperature for 16 hours.

After the completion of the reaction, the reaction mixture was extracted with ethyl acetate, and the extract was washed several times with saturated aqueous NaHCO$_3$ and water. The organic layer thus obtained was dried over Na$_2$SO$_4$, concentrated under a reduced pressure, and then purified by column chromatography (ethyl acetate:hexane=1:2) to obtain the title compound having two isopropylidene groups introduced to the backbone thereof, as a white foamy solid (6.03 g).

$^1$H NMR (CDCl$_3$): δ 1.44-1.55 (m, 12H), 3.67-3.95 (m, 4H), 4.10-4.16 (m, 1H), 5.43 (dd, J=7.9, 10.4 Hz, 1H, for 3a), 5.60 (t, J=9.2 Hz, 1H, for 3b), 7.42-7.49 (m, 2H), 7.54-7.62 (m, 1H), 8.07-8.10 (m, 2H).

<1-2> Introduction of t-Butyldimethylsilane (TBS) Protecting Group

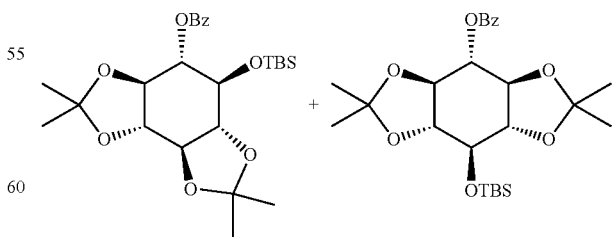

The compound obtained in Preparative Example <1-1> (646 mg, 1.77 mmol) was dissolved in N,N-dimethylformamide (3 ml), and imidazole (534 mg, 3.54 mmol) and t-butyldimethylsilyl chloride (534 mg, 3.54 mmol) were added thereto at 0° C. The mixture thus obtained, was warmed to room temperature, and then stirred for 10 hours.

After the completion of the reaction, the reaction mixture was extracted with ethyl acetate, and the extract was washed several times with water and saturated aqueous NaHCO$_3$. The organic layer thus obtained was dried over Na$_2$SO$_4$, concentrated under a reduced pressure, and then purified by column chromatography (ethyl acetate:hexane=1:3) to obtain the title compound as a white solid (750 mg).

$^1$H NMR (CDCl$_3$): δ 0.07, 0.06 (2s, 6H, for 4a), 0.14 (s, 6H, for 4b), 0.73 (s, 9H, for 4a), 0.92 (s, 9H, for 4b), 1.41-1.46 (m, 12H), 3.60-4.10 (m, 5H), 5.47-5.56 (m, 1H), 7.41-7.46 (m, 2H), 7.54-7.56 (m, 1H), 8.00-8.09 (m, 2H).

<1-3> Removal of Benzoyl (Bz) Protecting Group

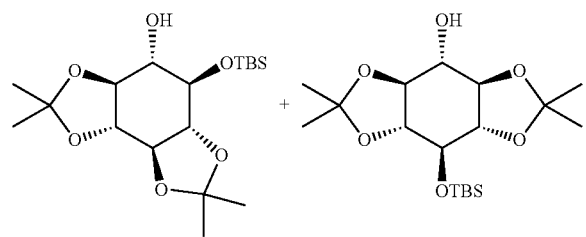

The compound obtained in Preparative Example <1-2> (700 mg, 1.46 mmol) was dissolved in a mixture of methanol and dichloromethane (1:4) (2.5 ml), a NaOMe solution (134 μl, 0.58 mmol, 25 wt %) was added thereto, and the mixture thus obtained was refluxed for 3 hours.

Thereafter, the mixture was cooled to room temperature, diluted with dichloromethane, filtered through silica gel, and concentrated. The concentrate thus obtained was washed with a mixture of hexane and ethyl acetate (19:1), and then dried in a vacuum to obtain the title compound as a white solid (547 mg).

$^1$H NMR (CDCl$_3$): δ 0.07-0.13 (m, 6H), 0.85-0.90 (m, 9H), 1.40-1.46 (m, 12H), 3.43-3.78 (m, 6H).

<1-4> Introduction of Carbobenzoxy (Cbz)-Protected Linker

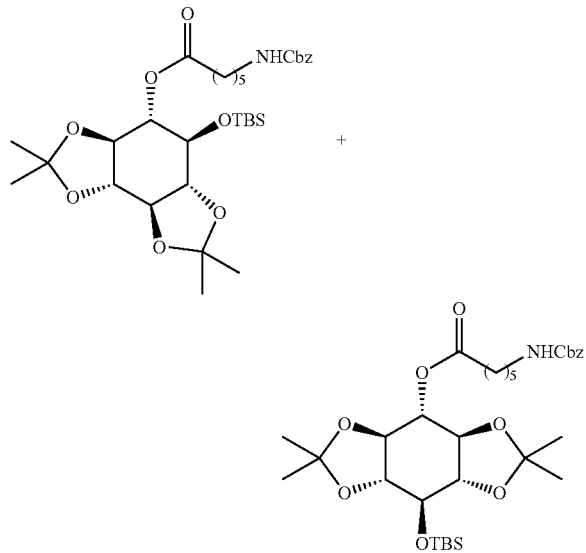

The compound obtained in Preparative Example <1-3> (360 mg, 0.960 mmol), 6-benzoyloxycarbonylaminohexanoic acid (290 mg, 1.15 mmol), 1-ethyl-3-(3-dimethylaminopropyl)carbodiimide (221 mg, 1.15 mmol), and 4-dimethylaminopyridine (35 mg, 0.288 mmol) were dissolved in dichloromethane (3 ml) and stirred at room temperature for 24 hours.

After the completion of the reaction, the reaction mixture was extracted with ethyl acetate, and the extract was washed several times with saturated aqueous NaHCO$_3$ and water. The organic layer thus obtained was dried over Na$_2$SO$_4$, concentrated under a reduced pressure, and then purified by column chromatography (ethyl acetate:hexane=1:3) to obtain the title compound as a sticky liquid (485 mg).

$^1$H NMR (CDCl$_3$): δ 0.05 (s, 3H, for 6a), 0.08 (s, 3H, for 6a), 0.11 (s, 6H, for 6b), 0.84 (s, 9H, for 6a), 0.90 (s, 9H, for 6b), 1.37-1.53 (m, 16H), 1.63-1.68 (m, 2H), 2.32-2.39 (m, 2H), 3.15-3.19 (m, 2H), 3.50-3.62 (m, 2H), 3.63-3.68 (m, 1H), 3.71-3.79 (m, 1H), 3.89 (dd, J=7.8, 10.0 Hz, 1H), 4.81 (brs, 1H), 5.08 (s, 2H), 5.22 (dd, J=7.8, 10.7 Hz, 1H), 7.30-7.36 (m, 5H).

<1-5> Removal of Acetonide Protecting Group and t-Butyldimethylsilane Protecting Group

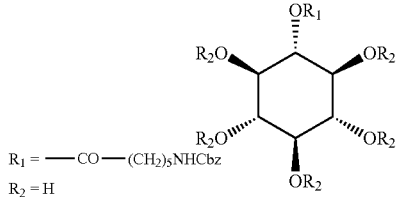

The compound obtained in Preparative Example <1-4> (310 mg, 0.5 mmol) was dissolved in a mixture of dichloromethane and methanol (1:4, 2 ml), a HCl gas-saturated ethyl acetate solution (1 ml) was added thereto, and the mixture thus obtained was stirred at room temperature for 30 min.

After the completion of the reaction, the reaction mixture was concentrated under a reduced pressure to completely remove the solvent, washed with hexane and ether, and dried in a vacuum to obtain the title compound as a white solid (225 mg).

$^1$H NMR (D$_2$O): δ 1.33-1.37 (m, 2H), 1.48-1.53 (m, 2H), 1.62-1.67 (m, 2H), 2.46 (t, J=7.1 Hz, 2H), 3.12 (t, J=6.0 Hz, 2H), 3.34-3.50 (m, 6H), 5.12 (s, 2H), 7.42-7.44 (m, 5H).

Preparative Example 2

Preparation of Scyllo-Inositol Having Benzoyl (Bz)-Protected OH Group and Carbobenzoxy (Cbz)-Protected Linker <2-1> Introduction of Carbobenzoxy (Cbz)-Protected Linker

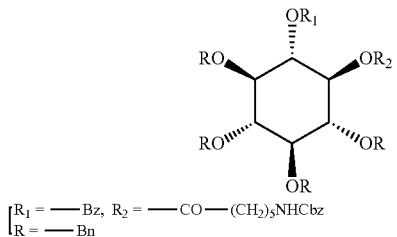

1-O-benzoyl-2,3,4,5-tetrabenzyl-scyllo-inositol (Korean Patent No. 578732; 2.5 g, 3.88 mmol), 6-benzoyloxycarbonylaminohexanoic acid (1.5 mg, 5.65 mmol), 1-ethyl-3-(3-dimethylaminopropyl)carbodiimide (1.1 mg, 5.65 mmol) and 4-dimethylaminopyridine (140 mg, 1.14 mmol) were dissolved in dichloromethane (20 ml) and stirred at room temperature for 24 hours.

After the completion of the reaction, the reaction mixture was extracted with ethyl acetate, and the extract was washed several times with saturated aqueous $NaHCO_3$ and water. The organic layer thus obtained was dried over $Na_2SO_4$, concentrated under a reduced pressure, and then purified by column chromatography (ethyl acetate:hexane=1:3) to obtain the title compound as a white solid (3.38 g).

$^1$H NMR (CDCl$_3$): δ 0.91-1.29 (m, 6H), 2.01 (t, J=7.1 Hz, 2H), 2.88 (br. s, 2H), 3.66-3.70 (m, 4H), 4.56-4.88 (m, 8H), 5.08 (s, 2H), 5.27-5.37 (m, 2H), 7.03-7.53 (m, 28H), 7.94 (d, J=7.2 Hz, 2H).

<2-2> Removal of Benzyl (Bn) Protecting Group and Carbobenzoxy (Cbz) Protecting Group

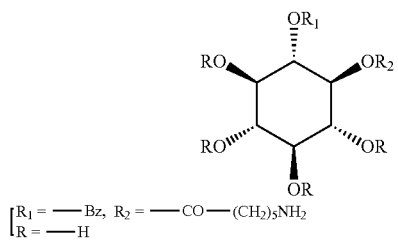

The compound obtained in Preparative Example <2-1> (3.38 g, 3.79 mmol) was dissolved in a mixture of dichloromethane and ethanol (1:1.5, 50 ml), and Pd(OH)$_2$/C (20 wt %) (1.7 g) was added thereto. The mixture thus obtained was stirred at room temperature under H$_2$ gas (4 atm) for one day and filtered through celite to remove Pd(OH)$_2$/C. The filtrate thus obtained was concentrated under a reduced pressure to obtain the title compound as a white sticky solid (1.4 g).

$^1$H NMR (CD$_3$OD): δ 1.09-1.20 (m, 2H), 1.37-1.50 (m, 4H), 2.14-2.35 (m, 2H), 2.67 (t, J=7.7 Hz, 2H), 3.38-3.45 (m, 2H), 3.54-3.67 (m, 2H), 5.12-5.25 (m, 2H), 7.47-7.52 (m, 2H), 7.61-7.63 (m, 1H), 8.00-8.03 (m, 2H).

<2-3> Re-Introduction of Carbobenzoxy (Cbz) Protecting Group

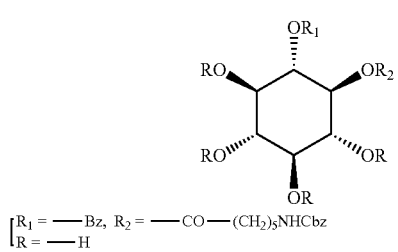

The compound obtained in Preparative Example <2-2> (1.3 g, 3.52 mmol) was dissolved in a mixture of 1,4-dioxane and water (1:1, 20 ml). Triethylamine (594 μl, 4.22 mmol) was added thereto, and carbobenzoxy chloride (Cbz-Cl) (980 μl, 7.04 mmol) was added dropwise at 0° C. for 30 min. The obtained mixture was stirred at room temperature for 12 hours, concentrated under a reduced pressure. The water (20 ml) was added to the obtained concentrates and extracted with ethyl acetate. The organic layer thus obtained was dried over Na$_2$SO$_4$, concentrated under a reduced pressure, and then purified by column chromatography (dichloromethane: methanol=12:1) to obtain the title compound as a white foamy solid (1.2 g).

$^1$H NMR (CD$_3$OD): δ 1.04-1.36 (m, 6H), 2.14-2.23 (m, 2H), 2.86-2.89 (m, 2H), 3.38-3.41 (m, 2H), 3.52-3.62 (m, 2H), 5.05 (s, 2H), 5.10-5.20 (m, 2H), 7.35-7.57 (m, 8H), 7.99-8.01 (m, 2H).

Preparative Example 3

Preparation of Scyllo-Inositol Having the Same Two Neighboring Protecting Groups <3-1> Introduction of Benzoyl (Bz) Protecting Group

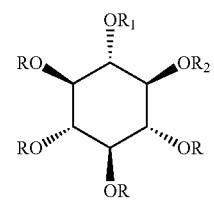

1-O-benzoyl-2,3,4,5-tetrabenzyl-scyllo-inositol (Korean Patent No. 578732; 150 mg, 0.233 mmol) was dissolved in pyridine (3 ml), benzoyl chloride (35 μl, 0.302 mmol) was added dropwise thereto, and the mixture thus obtained was stirred at 60° C. for 24 hours.

After the completion of the reaction, water (5 ml) was added to the reaction mixture, stirred for 30 min, diluted with ethyl acetate, and the extract was washed with HCl (1M), NaHCO$_3$ and Na$_2$SO$_4$. The organic layer thus obtained was dried over Na$_2$SO$_4$, concentrated under a reduced pressure, and then purified by column chromatography (ethyl acetate: hexane=1:2) to obtain the title compound having two benzoyl groups as a white solid (174 mg).

$^1$H NMR (CDCl$_3$): δ 3.8-3.82 (m, 4H), 4.63-4.80 (dd, 4H), 4.93 (s, 4H), 5.55-5.57 (m, 2H), 7.05-7.90 (m, 30H).

<3-2> Removal of Benzyl (Bn) Protecting Group

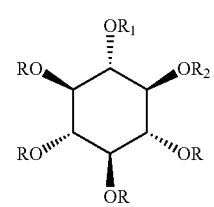

The compound obtained in Preparative Example <3-1> (160 mg, 0.214 mmol) was dissolved in a mixture of dichloromethane and ethanol (1:2, 12 ml) and Pd(OH)$_2$/C (20 wt %, 75 mg) was added thereto. The mixture thus obtained was stirred at room temperature under H$_2$ gas (4 atm) for one day, and filtered through celite to remove Pd(OH)$_2$/C. The filtrate thus obtained was concentrated under a reduced pressure to obtain the title compound as a white solid compound (94 mg).

$^1$H NMR (CD$_3$OD): δ 3.45-3.48 (m, 2H), 3.68-3.74 (m, 2H), 5.34-5.39 (m, 2H), 7.33-7.90 (m, 10H).

Preparative Example 4

Preparation of Trehalose Having the Same Two Protecting Groups

<4-1> Introduction of Trityl (Tr) Protecting Group

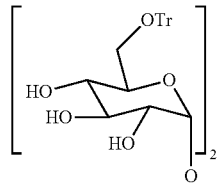

Trehalose hydrate (2.2 g, 5.82 mmol) and trityl chloride (7.7 g, 27.21 mmol) were dissolved in pyridine (40 ml) at room temperature and stirred for 5 hours while being slowly heated to 60° C.

After the completion of the reaction, the reaction mixture was diluted with ethyl acetate and the extract was washed with aqueous hydrochloric acid (1N) and saturated aqueous $NaHCO_3$. Thereafter, aqueous NaCl was added dropwise thereto to obtain a suspension. The suspension was filtered using a Buchner funnel. The filtrate thus obtained was washed with diethylether, and dried under a reduced pressure to obtain a white compound (4.37 g).

m.p. 275-276° C. (dec.)

$^1$H NMR (in MeOD, δ) 3.37 (app. t, 6H, J=3.8 Hz), 3.57 (dd, 2H, J=9.7 and 3.8 Hz), 3.79 (app. t, 2H, J=9.3 Hz), 4.02-4.09 (m, 2H), 5.36 (d, 2H, J=3.8 Hz, anomeric protons), 7.14-7.25 (m, 18H, trityl protons), 7.41-7.52 (m, 12H, trityl protons).

Preparative Example 5

Preparation of Glucose Derivative Having Carbobenzoxy (Cbz)-Protected Linker <5-1> Preparation of Penta-O-Benzoyl-D-Glucose

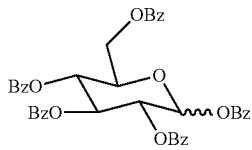

D-glucose (2.0 g, 11 mmol) was dissolved in anhydrous pyridine (24 ml), and acetic anhydride (8 ml, 67 mmol) was added thereto, and the mixture thus obtained was stirred at 60~65° C. for 3 hours.

After the completion of the reaction, the reaction mixture was extracted with dichloromethane, and the extract was washed with 1N HCl, saturated aqueous $NaHCO_3$ and aqueous NaCl. The product thus obtained was dried over $Na_2SO_4$, concentrated under a reduced pressure, and then recrystallized from methanol/acetone to obtain the title compound as a white solid (5.7 g).

$^1$H NMR (CDCl$_3$): δ 4.40-4.46 (m, 1H, H-5), 4.49 (dd, J=12.23 Hz, 4.70 Hz, 1H, H-6b), 4.65 (dd, J=12.31 Hz, 2.82 Hz, 1H, H-6a), 5.82-5.91 (m, 2H, H-2, H-4), 6.07 (t, J=9.4 Hz, 1H, H-3), 6.31 (d, J=7.99 Hz, 1H, H-1), 7.24-8.05 (m, 25H, arom).

<5-2> Preparation of 2,3,4,6-tetra-O-Benzoyl-D-Glucose

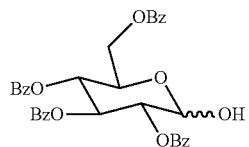

The compound obtained Preparation Example <5-1> (2.0 g, 2.8 mmol) was dissolved in dichloromethane (10 ml), and hydrobromic acid was added thereto at 0° C., and the mixture thus obtained was stirred at room temperature for 7 hours.

After the reaction was completed using ice water, the reaction mixture was extracted with dichloromethane, and the extract was washed with saturated aqueous $NaHCO_3$ and aqueous NaCl. The product thus obtained was dried over $Na_2SO_4$ and concentrated under a reduced pressure. The concentrate thus obtained was dissolved in acetone/water (6 ml/0.3 ml). $Ag_2CO_3$ was added thereto, and the mixture thus obtained was stirred at room temperature for 3 hours.

After the completion of the reaction, the reaction mixture was filtered through celite to remove $Ag_2CO_3$. The filtrate thus obtained was concentrated under a reduced pressure, to obtain the title compound as a white sticky solid (1.7 g).

$^1$H NMR (CDCl$_3$): δ 4.16-4.20 (m, 1H, H-5), 4.46 (dd, J=12.24 Hz, 4.99 Hz, 1H, H-6b), 4.61 (dd, J=12.16 Hz, 2.91 Hz, 1H, H-6a), 5.05 (d, J=7.93 Hz, 1H, H-1), 5.32 (t, J=8.0 Hz, 1H, H-2), 5.67 (t, J=9.7 Hz, 1H, H-4), 5.93 (t, J=9.7 Hz, 1H, H-3), 7.24-8.03 (m, 20H, arom).

<5-3> Preparation of 2,3,4,6-tetra-O-Benzoyl-D-Glucose Acetimidate

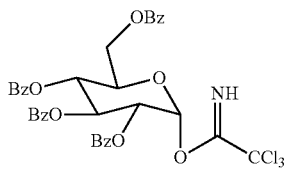

The compound obtained in Preparation Example <5-2> (1.5 g, 2.6 mmol) was dissolved in dichloromethane (10 ml). 1,8-diazabicyclo[5,4,0]undec-7-ene (DBU) (20 μl, 0.13 mmol) and trichloroacetonitrile (2.6 ml, 26.1 mmol) was added thereto at 0° C., and the mixture was stirred for 4 hours.

After the completion of the reaction, the reaction mixture was concentrated under a reduced pressure, and then purified by column chromatography (ethyl acetate:hexane=1:3) to obtain the title compound as a white solid (1.2 g).

$^1$H NMR (CDCl$_3$): δ 4.46 (dd, J=12.9 Hz, 5.4 Hz, 1H, H-6b), 4.16-4.20 (m, 2H, H-5, H-6a), 5.60 (dd, J=10.2 Hz, 3.7 Hz, 1H, H-2), 5.83 (t, J=9.8 Hz, 1H, H-4), 6.28 (t, J=10.0

Hz, 1H, H-3), 6.84 (d, J=3.7 Hz, 1H, H-1), 5.93 (t, J=9.7 Hz, 1H, H-3), 7.26-8.05 (m, 20H, arom), 8.64 (s, 1H, NH).

<5-4> Preparation of 1-O—(N-Carbobenzoxy-6-Aminopentyl)-2,3,4,6-tetra-O-Benzoyl-D-Glucopyranoside

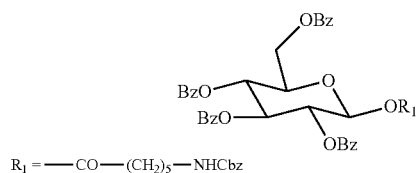

$R_1 = \text{—CO—(CH}_2)_5\text{—NHCbz}$

N-carbobenzoxy-6-aminopentanol (0.32 g, 1.35 mmol) and trimethylsilyl trifluoromethanesulfonate (0.25 ml, 1.35 mmol) were dissolved in dichloromethane (10 ml) and cooled to 0° C. To this solution, was added a solution obtained by dissolving the compound obtained in Preparative Example <5-3> (1 g, 1.4 mmol) in dichloromethane (25 ml), and the mixture thus obtained was stirred for 2 hours.

After the completion of the reaction, the reaction mixture was filtered through celite. The filtrate thus obtained was washed with saturated aqueous NaHCO$_3$ and aqueous NaCl. The product thus obtained was dried over Na$_2$SO$_4$, concentrated under a reduced pressure, and then purified by column chromatography (ethyl acetate:hexane=1:2) to obtain the title compound as a transparent sticky oil (0.8 g).

$^1$H NMR (CDCl$_3$): δ 1.20-1.54 (m, 6H), 2.93-2.95 (d, J=6.1 Hz, 2H), 3.51-3.54 (m, 1H), 3.88-3.95 (m, 1H), 4.10-4.17 (m, 1H, H-5), 4.47 (dd, J=12.2 Hz, 5.0 Hz, 1H, H-6b), 4.63 (d, J=11.9 Hz, 2H, H-6b, NH), 4.81 (d, J=7.7 Hz, 1H, H-1), 5.08 (s, 1H, benzyl), 5.52 (t, J=9.4 Hz, 1H, H-2), 5.68 (t, J=9.7 Hz, 1H, H-4), 5.91 (t, J=9.6 Hz, 1H, H-3), 7.26-8.03 (m, 25H, arom).

<5-5> Preparation of 1-O—(N-Carbobenzoxy-6-Aminopentyl)-D-Glucopyranose

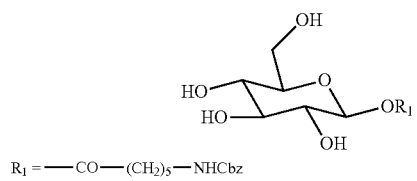

$R_1 = \text{—CO—(CH}_2)_5\text{—NHCbz}$

The compound obtained in Preparative Example <5-4> (0.8 g, 1.0 mmol) was dissolved in methanol (30 ml), a solution (30 μl, 0.1 mmol) of sodium methoxide in methanol was added thereto, and the mixture thus obtained was stirred at 70° C. for 3 hours.

After the completion of the reaction, the reaction mixture was neutralized with acidic cation exchange resin (Dowex 50WX8-100), and then concentrated under a reduced pressure to obtain the title compound as a colorless sticky solid (369 mg).

$^1$H-NMR (CD$_3$OD): δ 1.35-1.58 (m, 6H), 3.03-3.27 (m, J=6.1 Hz 5H), 3.44-3.49 (m, 1H), 3.59-3.64 (m, 1H), 3.80-3.85 (m, 3H), 4.18 (d, J=7.7 Hz, 1H), 5.00 (s, 1H, benzyl), 5.52 (t, J=9.4 Hz, 1H, H-2), 5.68 (t, J=9.7 Hz, 1H, H-4), 5.91 (t, J=9.6 Hz, 1H, H-3), 7.29 (brs, 5H, arom).

Example 1

Preparation of Scyllo-Inositol Derivative Having Ten Guanidine Groups

<1-1> Introduction of Side Chain to Scyllo-Inositol by Acylation

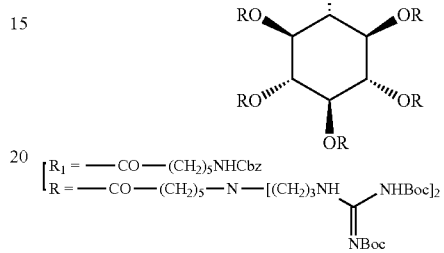

$R_1 = \text{—CO—(CH}_2)_5\text{NHCbz}$
$R = \text{—CO—(CH}_2)_5\text{—N—[(CH}_2)_3\text{NH}\underset{\text{NBoc}}{\diagup}\text{NHBoc]}_2$ The compound having five OH groups obtained in Preparative Example <1-5> (34 mg, 0.079 mmol), a branched linker having two guanidine groups (Korean Patent No. 699279; 464 mg, 0.636 mmol), 1-ethyl-3-(3-dimethylaminopropyl) carbodiimide (151 mg, 0.79 mmol) and 4-dimethylaminopyridine (24 mg, 0.2 mmol) were dissolved in N,N-dimethylformamide (2 ml), and stirred at room temperature for two days.

After the completion of the reaction, the reaction mixture was washed several times with water and aqueous NaHCO$_3$. The organic layer thus obtained was dried over Na$_2$SO$_4$, concentrated under a reduced pressure, and then purified by column chromatography (dichloromethane:methanol=10:1) to obtain the title compound having five acyl side chains, as a sticky solid (228 mg).

$^1$H NMR (CDCl$_3$): δ 1.25-1.69 (m, 236H), 2.16-2.25 (m, 12H), 2.30-2.46 (m, 30H), 3.14 (m, 2H), 3.43-3.44 (m, 18H), 5.07 (s, 2H), 5.23 (s, 6H), 7.33 (m, 5H), 8.50 (m, 10H), 11.49 (s, 10H).

<1-2> Removal of Carbobenzoxy (Cbz) Protecting Group from Terminal Amine Group of Linker

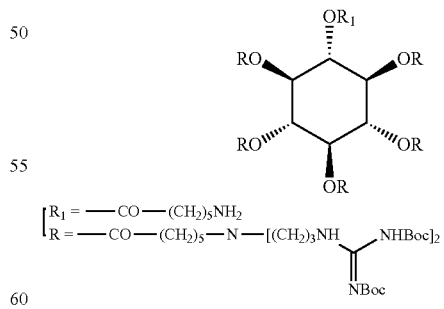

$R_1 = \text{—CO—(CH}_2)_5\text{NH}_2$
$R = \text{—CO—(CH}_2)_5\text{—N—[(CH}_2)_3\text{NH}\underset{\text{NBoc}}{\diagup}\text{NHBoc]}_2$ The compound obtained in Example <1-1> (100 mg, 0.025 mmol) was dissolved in a mixture of methanol and dichloromethane (9:1) (3 ml), and Pd/C (10 wt %, 50 mg) was added thereto. The mixture thus obtained was stirred at room temperature under H$_2$ gas (1 atm) for one day, and filtered through celite to remove Pd/C. The filtrate thus obtained was concentrated under a reduced pressure to obtain the title compound as a white sticky solid (95 mg).

$^1$H NMR (CDCl$_3$): δ 1.21-2.24 (m, 248H), 2.88-3.70 (m, 50H), 5.23-5.27 (m, 6H), 8.47 (s, 10H), 11.43 (m, 10H).

<1-3> Introduction of Fluorescence Probe (FITC)

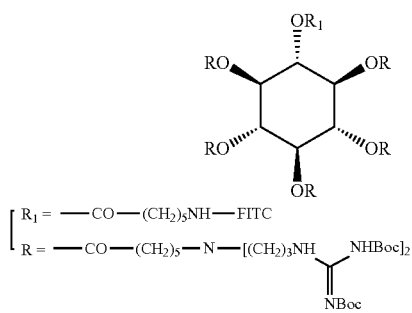

The compound obtained in Example <1-2> (85 mg, 0.022 mmol) was dissolved in a mixture of tetrahydrofuran and ethanol (3:2) (0.675 ml), fluorescein-5-isocyanate (10.3 mg, 0.026 mmol) and triethylamine (9.1 µl, 0.067 mmol) were added thereto, and the mixture thus obtained was stirred at room temperature for one day.

After the completion of the reaction, the reaction mixture was concentrated under a reduced pressure, and then purified by column chromatography (dichloromethane:methanol=10: 1) to obtain a dark yellow sticky compound (100 mg).

$^1$H NMR (CDCl$_3$): δ 1.14-1.89 (m, 236H), 2.14-3.05 (m, 42H), 3.39-3.42 (m, 20H), 5.22 (s, 6H), 6.58-6.94 (m, 6H), 7.80-8.05 (m, 3H), 8.45 (s, 10H), 11.38 (s, 10H).

<1-4> Removal of N-Boc Protecting Group from N,N'-di-Butyloxycarbonyl (Boc)-Guanidine Group

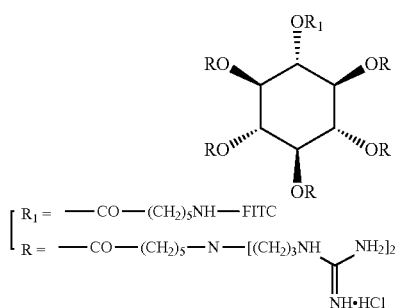

The compound obtained in Example <1-3> (100 mg) was dissolved in ethyl acetate (1 ml), HCl gas-saturated ethyl acetate (2 ml) was added dropwise thereto, and the mixture thus obtained stirred at room temperature for one day.

After the completion of the reaction, the reaction mixture was concentrated under a reduced pressure to remove the solvent, and washed with ethyl acetate to remove non-polar impurities. Thereafter, purification by MPLC chromatography (0.1% trifluoroacetic acid-containing water:acetonitrile=1:1 to 1:2) was performed to obtain a light green compound (35 mg).

$^1$H NMR (CD$_3$OD): δ 1.28-2.40 (m, 72H), 3.30-3.42 (m, 48H), 5.48 (s, 6H), 7.14-8.56 (m, 9H).

Example 2

Preparation of Scyllo-Inositol Derivative Having Five Guanidine Groups

<2-1> Introduction of Side Chain to Scyllo-Inositol by Acylation

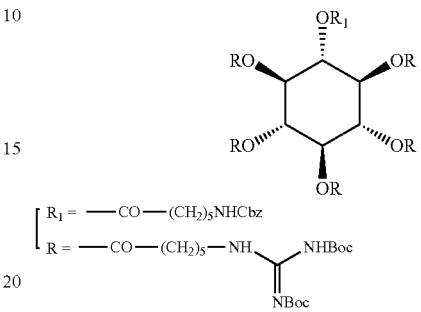

The compound having five OH groups obtained in Preparative Example <1-5> (85.8 mg, 0.2 mmol), a linear linker having a single guanidine group (600 mg, 1.6 mmol), 1-ethyl-3-(3-dimethylaminopropyl)carbodiimide (383.42 mg, 2 mmol) and 4-dimethylaminopyridine (61 mg, 0.5 mmol) were dissolved in N,N-dimethylformamide (2 ml) and stirred at room temperature for two days.

After the completion of the reaction, the reaction mixture was washed several times with water and aqueous NaHCO$_3$. The organic layer thus obtained was dried over Na$_2$SO$_4$, concentrated under a reduced pressure, and then purified by column chromatography (dichloromethane:methanol=10:1) to obtain the title compound having five acyl side chains, as a sticky solid (402 mg).

$^1$H NMR (CDCl$_3$, 500 MHz): δ 1.28-1.38 (m, 12H), 1.47-1.62 (m, 114H), 2.22-2.42 (m, 12H), 3.18-3.21 (m, 2H), 3.37-3.43 (m, 10H), 5.10 (s, 2H), 5.11-5.13 (m, 1H), 5.25 (s, 5H), 7.29-7.36 (m, 5H), 8.29-8.32 (t, J=5.0 Hz, 5H), 11.51 (s, 5H).

<2-2> Removal of Carbobenzoxy (Cbz) Protecting Group from Terminal Amine Group of the Linker

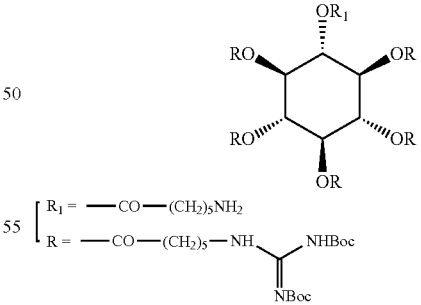

The compound obtained in Example <2-1> (100 mg, 0.025 mmol) was dissolved in a mixture of methanol and dichloromethane (9:1) (3 ml) and Pd/C (10 wt %, 50 mg) was added thereto. The mixture thus obtained was stirred at room temperature under H$_2$ gas (1 atm) for one day and filtered through celite to remove Pd/C. The filtrate thus obtained was concentrated under a reduced pressure to obtain the title compound as a white sticky solid (87 mg).

¹H NMR (CDCl₃): δ 1.25-1.56 (m, 126H), 2.21 (t, J=6.8 Hz, 12H), 2.92-2.99 (m, 2H), 3.36-3.48 (m, 10H), 5.23 (s, 6H), 8.29-8.36 (m, 5H), 11.5 (m, 5H).

<2-3> Introduction of Fluorescence Probe (FITC)

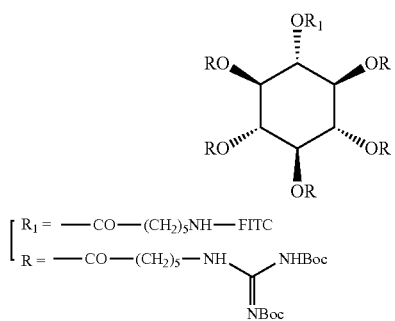

The compound obtained in Example <2-2> (85 mg, 0.04 mmol) was dissolved in a mixture of tetrahydrofuran and ethanol (3:2) (0.675 ml), and fluorescein-5-isocyanate (19.1 mg, 0.049 mmol) and triethylamine (17.1 μl, 0.123 mmol) were added thereto, and stirred at room temperature for one day.

After the completion of the reaction, the reaction mixture was concentrated under a reduced pressure, and then purified by column chromatography (dichloromethane:methanol=10:1) to obtain a dark yellow sticky compound (104 mg).

¹H NMR (CDCl₃): δ 1.23-1.49 (m, 126H), 2.11-2.25 (m, 12H), 3.05-3.75 (m, 12H), 5.24 (s, 6H), 6.55-7.11 (m, 6H), 7.95-8.17 (m, 3H), 8.35-8.41 (m, 5H), 11.5 (m, 5H).

<2-4> Removal of N-Boc Protecting Group from N,N'-di-Butyloxycarbonyl (Boc)-Guanidine Group

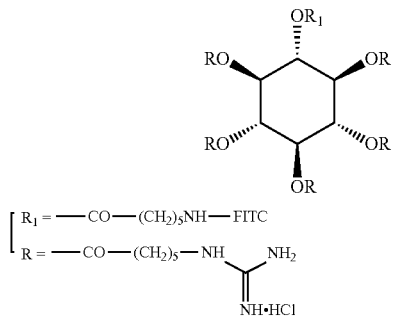

The compound obtained in Example <2-3> (104 mg) was dissolved in ethyl acetate (1 ml), HCl gas-saturated ethyl acetate (2 ml) was added dropwise thereto, and the mixture thus obtained was stirred at room temperature for one day.

After the completion of the reaction, the reaction mixture was concentrated under a reduced pressure to remove the solvent, and washed with ethyl acetate to remove non-polar impurities. Subsequently, purification by MPLC chromatography (0.1% trifluoroacetic acid-containing water:acetonitrile=1:1~1:2) was performed to obtain a light green compound (42 mg).

¹H NMR (CD₃OD): δ 1.23-1.38 (m, 12H), 1.58-1.72 (m, 24H), 2.23-2.32 (m, 12H), 3.06-3.15 (m, 10H), 3.61 (m, 1H), 3.94 (m, 1H), 5.43 (s, 6H), 6.54-6.74 (m, 6H), 7.15-7.18 (m, 1H), 7.70-7.73 (m, 1H), 8.01-8.25 (m, 1H).

Example 3

Preparation of Scyllo-Inositol Derivative Having Eight Guanidine Groups and FITC <3-1> Introduction of Side Chain to Scyllo-Inositol by Acylation

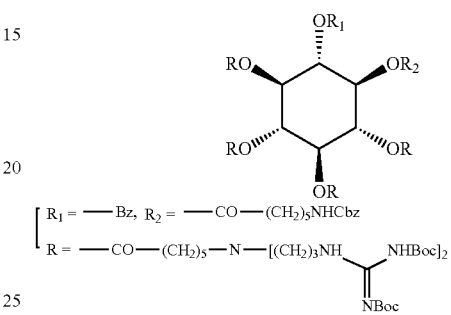

The compound obtained in Preparative Example <2-3> (300 mg, 0.59 mmol), a branched linker having two guanidine groups (Korean Patent No. 699279; 2.61 g, 3.57 mmol), 1-ethyl-3-(3-dimethylaminopropyl)carbodiimide (684 mg, 3.57 mmol) and 4-dimethylaminopyridine (87 mg, 0.71 mmol) were dissolved in N,N-dimethylformamide (3 ml), and stirred at room temperature for three days.

After the completion of the reaction, the reaction mixture was washed several times with water and aqueous NaHCO₃. The organic layer thus obtained was dried over Na₂SO₄, concentrated under a reduced pressure, and then purified by column chromatography (dichloromethane:methanol=10:1) to obtain the title compound as a sticky solid (1.85 g).

¹H NMR (CDCl₃): δ 0.91-1.69 (m, 190H), 2.10-2.46 (m, 32H), 2.90-2.95 (m, 4H), 3.38-4.22 (m, 16H), 4.88-5.51 (m, 6H), 5.07 (s, 2H), 7.30-7.36 (m, 5H), 7.39-7.45 (m, 2H), 7.54-7.60 (m, 1H), 7.91-7.95 (m, 2H), 8.49 (brs, 8H), 11.49 (brs, 8H).

<3-2> Removal of Carbobenzoxy (Cbz) Protecting Group from Terminal Amine Group of the Linker

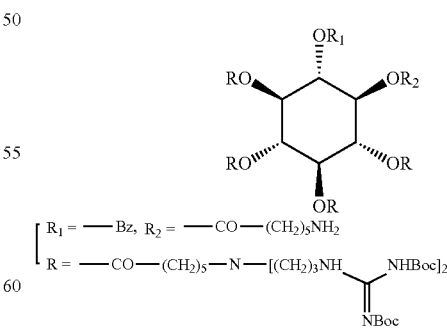

The compound obtained in Example <3-1> (1 g, 0.296 mmol) was dissolved in a mixture of methanol and dichloromethane (9:1) (25 ml) and Pd/C (10 wt %, 500 mg) was added thereto. The mixture thus obtained was stirred at room temperature under H₂ gas (4 atm) for one day, and filtered through celite to remove Pd/C. The filtrate thus obtained was concentrated under a reduced pressure to obtain the title compound as a white sticky solid (960 mg).

$^1$H NMR (CDCl$_3$): δ 1.06-2.26 (m, 202H), 2.88-3.70 (m, 40H), 5.31-5.56 (m, 6H), 7.45-7.50 (m, 2H), 7.61-7.64 (m, 1H), 7.93-7.95 (m, 2H), 8.47 (s, 8H), 11.43 (m, 8H).

<3-3> Introduction of Fluorescence Probe (FITC)

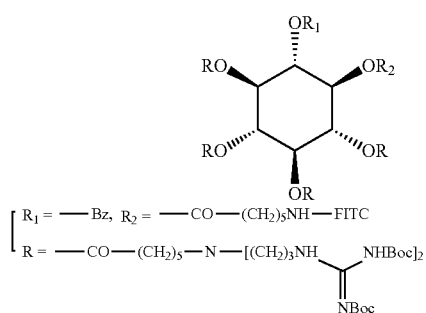

The compound obtained in Example <3-2> (879 mg, 0.27 mmol) was dissolved in a mixture of tetrahydrofuran and ethanol (3:1) (5 ml), fluorescein-5-isocyanate (127 mg, 0.325 mmol), triethylamine (113 μl, 0.81 mmol) were added thereto, and the mixture thus obtained was stirred at room temperature for one day.

After the completion of the reaction, the reaction mixture was concentrated under a reduced pressure, and then purified by column chromatography (dichloromethane:methanol=10:1) to obtain a dark yellow sticky compound (888 mg).

$^1$H NMR (CDCl$_3$): δ 1.02-2.88 (m, 226H), 3.32-3.51 (m, 16H), 3.62-4.12 (m, 2H), 5.05-5.61 (m, 6H), 6.56-7.90 (m, 14H), 8.50 (brs, 8H), 11.44 (brs, 8H).

<3-4> Removal of N-Boc Protecting Group from N,N'-di-Butyloxycarbonyl (Boc)-Guanidine Group

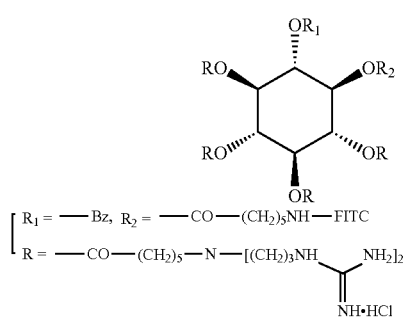

HCl gas-saturated ethyl acetate (10 ml) was added dropwise to the compound obtained in Example <3-3> (888 mg), and the solution thus obtained was stirred at room temperature for one day.

After the completion of the reaction, the reaction mixture was concentrated under a reduced pressure, and washed with ethyl acetate to remove non-polar impurities. Subsequently, purification by MPLC chromatography (0.1% trifluoroacetic acid-containing water:acetonitrile=1:1~1:2) was performed to obtain a light green compound (412 mg).

$^1$H NMR (CD$_3$OD): δ 1.15-2.38 (m, 80H), 2.88-3.66 (m, 16H), 5.56-5.72 (m, 6H), 7.20-7.70 (m, 10H), 7.91-8.59 (m, 4H).

Example 4

Preparation of Scyllo-Inositol Derivative Having Eight Guanidine Groups

<4-1> Introduction of Side Chain to scyllo-Inositol by Acylation

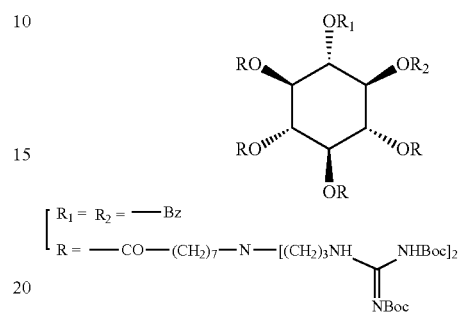

The compound obtained in Preparative Example <3-2> (30 mg, 0.0772 mmol), a branched linker having two guanidine groups (Korean Patent No. 699279; 451 mg, 0.618 mmol), 1-ethyl-3-(3-dimethylaminopropyl)carbodiimide (133 mg, 0.695 mmol), and 4-dimethylaminopyridine (19 mg, 0.154 mmol) were dissolved in dichloromethane (3 ml), and stirred at room temperature for three days.

After the completion of the reaction, the reaction mixture was washed several times with water and aqueous NaHCO$_3$. The organic layer thus obtained was dried over Na$_2$SO$_4$, concentrated under a reduced pressure, and then purified by column chromatography (dichloromethane:methanol=10:1) to obtain the title compound having four acyl side chains as a sticky solid (180 mg).

$^1$H NMR (CDCl$_3$): δ 1.33-1.69 (m, 184H), 2.11-2.13 (m, 8H), 2.22-2.47 (m, 24H), 3.41-3.44 (m, 16H), 5.37-5.39 (m, 2H), 5.47-5.52 (m, 2H), 5.64-5.66 (m, 2H), 7.33-7.36 (m, 4H), 7.47-7.52 (m, 2H), 7.83-7.84 (m, 4H), 8.24-8.46 (m, 8H), 11.47 (brs, 8H);

MS (MALDI-TOF): m/z 3233.606 (M+).

<4-2> Removal of N-Boc Protecting Group from N,N'-di-Butyloxycarbonyl (Boc)-Guanidine Group

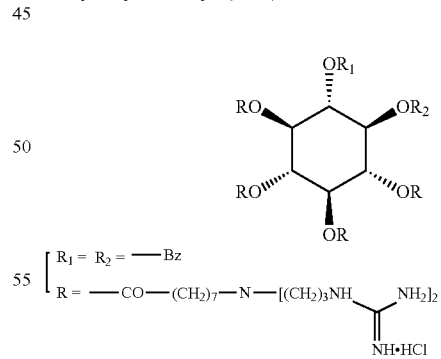

The compound obtained in Example <4-1> (80 mg, 0.0247 mmol) was dissolved in ethyl acetate (1 ml), HCl gas-saturated ethyl acetate (2 ml) was added dropwise thereto, and the mixture thus obtained was stirred at room temperature for one day.

After the completion of the reaction, the reaction mixture was concentrated under a reduced pressure to remove the solvent, and washed with ethyl acetate to remove non-polar impurities. Subsequently, purification by MPLC chromatography (0.1% trifluoroacetic acid-containing water:acetonitrile=70:30) was performed to obtain a light green compound (45 mg).

$^1$H NMR (CD$_3$OD): δ 1.25-2.45 (m, 48H), 3.07-3.49 (m, 40H), 5.70-5.72 (m, 2H), 5.80-5.87 (m, 2H), 5.96-5.98 (m, 2H), 7.49 (t, 4H, J=4.5 Hz), 7.65 (t, 2H, J=4.35 Hz), 7.92 (d, 4H, J=4.5 Hz);

MS (MALDI-TOF): m/z 1633.085 (M+).

Example 5

Preparation of Trehalose Derivative Having Six Guanidine Groups and FITC

<5-1> Introduction of Side Chain to Trehalose by Acylation

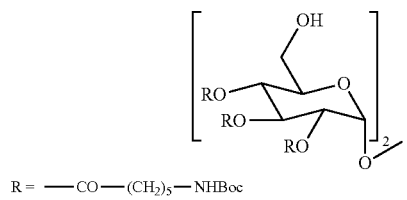

R = —CO—(CH$_2$)$_5$—NHBoc

The compound obtained in Preparative Example <4-1> (2.19 g, 2.65 mmol), N-butyloxycarbonyl (Boc)-6-aminohexanoic acid (5.52 g, 23.87 mmol), 1-ethyl-3-(3-dimethylaminopropyl)carbodiimide (4.58 g, 23.86 mmol), and 4-dimethylaminopyridine (0.97 g, 7.96 mmol) were dissolved in N,N-dimethylformamide (60 ml), and stirred at room temperature for 48 hours.

After the completion of the reaction, the reaction mixture was subjected to azeotropic distillation along with toluene at 60° C., diluted with aqueous lithium chloride (5%), extracted three times with ethyl acetate, and the extract was washed with saturated aqueous NaHCO$_3$. The organic layer thus obtained was dried over Na$_2$SO$_4$, concentrated under a reduced pressure, and then purified by column chromatography (ethyl acetate:hexane=1:1) to obtain the title compound as a yellow liquid (3.05 g).

$^1$H NMR (CDCl$_3$) δ 1.08-1.75 (m, 90H, CH$_3$ and NCH$_2$CH$_2$CH$_2$CH$_2$), 1.85-2.30 (m, 12H, CO—CH$_2$), 2.97-3.03 (m, 4H), 3.05-3.14 (m, 12H, NCH$_2$), 4.08-4.16 (m, 2H), 4.73-4.89 (m, 6H, NH), 5.10 (app. t, 2H, J=10.1 Hz), 5.23 (dd, 2H, J=10.2 and 3.8 Hz), 5.43-5.50 (m, 4H), 7.20-7.42 (m, 30H, trityl protons).

<5-2> Removal of N-Boc Protecting Group from Terminal Amino Group of the Side Chain

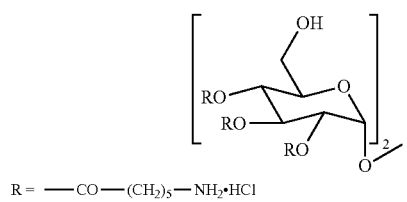

R = —CO—(CH$_2$)$_5$—NH$_2$·HCl

The compound obtained in Example <5-1> (625 mg, 0.30 μmol) was dissolved in HCl gas-saturated ethyl acetate (17 ml) and stirred at room temperature for two days.

After the completion of the reaction, the reaction mixture was concentrated under a reduced pressure to remove the solvent, and washed with ethyl acetate to remove non-polar impurities to obtain a white sticky compound (368 mg).

$^1$H NMR (MeOD) δ 1.39-1.72 (m, 36H, NCH$_2$CH$_2$CH$_2$CH$_2$), 2.29-2.49 (m, 12H, CO—CH$_2$), 2.91-3.11 (m, 12H, NCH$_2$), 3.56-3.69 (m, 3H), 3.80-3.95 (m, 2H), 4.16-4.42 (m, 2H), 4.90-5.10 (m, 3H), 5.24-5.54 (m, 4H).

<5-3> Conversion of Amino Group into N,N'-di-Boc-Guanidine Group

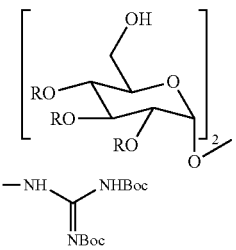

R = —CO—(CH$_2$)$_5$—NH\NHBoc
                              \\
                              NBoc

The compound obtained in Example <5-2> (358 mg, 0.29 mmol) was dissolved in a mixture of 1,4-dioxane and water (5:1, 5 ml), triethylamine (0.8 ml, 4.22 mmol) and N,N-di-Boc-N'-trifluoromethanesulfonylguanidine (1.63 g, 4.16 mmol) were added dropwise thereto, and the mixture was stirred at room temperature for three days.

After the completion of the reaction, the reaction mixture was concentrated under a reduced pressure, diluted with ethyl acetate, and the extract was washed with water and saturated aqueous NaCl. The product thus obtained was dried over Na$_2$SO$_4$, concentrated under a reduced pressure, and then purified by column chromatography (ethyl acetate:hexane=2:3) to obtain the title compound as a white solid (564 mg).

$^1$H NMR (CDCl$_3$) δ 1.36-1.75 (m, 144H, CH$_3$ and NCH$_2$CH$_2$CH$_2$CH$_2$), 2.25-2.38 (m, 12H, CO—CH$_2$), 3.30-3.45 (m, 12H, NCH$_2$), 3.62-3.70 (m, 4H), 4.25 (dd, 2H, J=11.8 and 5.0 Hz), 4.38-4.44 (m, 2H), 4.88 (dd, 2H, J=10.1 and 3.7 Hz), 5.31 (d, 2H, J=3.7 Hz, anomeric protons), 5.39 (app. t, 2H, J=9.9 Hz), 8.31 (br s, 6H), 11.49 (br s, 6H).

<5-4> Introduction of Carbobenzoxy (Cbz)-Protected Linker

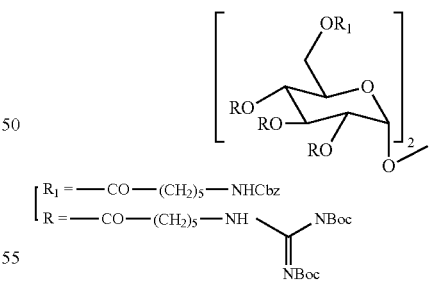

R$_1$ = —CO—(CH$_2$)$_5$—NHCbz
R = —CO—(CH$_2$)$_5$—NH\NBoc
                        \\
                        NBoc

The compound obtained in Example <5-3> (397 mg, 0.16 mmol), 6-benzyloxycarbonylaminohexanoic acid (512 mg, 1.92 mmol), 1-ethyl-3-(3-dimethylaminopropyl)carbodiimide (370 mg, 1.93 mmol) and 4-dimethylaminopyridine (47 mg, 0.38 mmol) were dissolved in N,N-dimethylformamide (10 ml) and stirred at room temperature for 48 hours.

After the completion of the reaction, the reaction mixture was diluted with aqueous lithium chloride (5%), and extracted three times with ethyl acetate. The product thus obtained was dried over Na$_2$SO$_4$, concentrated under a reduced pressure, and then purified by column chromatography (dichloromethane:methanol=50:1) to obtain a colorless sticky compound (313 mg).

$^1$H NMR (CDCl$_3$) δ 1.23-1.73 (m, 156H, CH$_3$ and NCH$_2$CH$_2$CH$_2$CH$_2$), 2.21-2.39 (m, 16H, CO—CH$_2$), 3.10-3.24 (m, 4H, CH$_2$NH—CO), 3.35-3.45 (m, 12H, CH$_2$NHCN), 3.90-4.05 (m, 4H), 4.17-4.29 (m, 2H), 4.97-5.18 (m, 8H), 5.24-5.37 (m, 4H), 5.47 (app. t, 2H, J=9.7 Hz), 7.28-7.39 (m, 10H, benzene protons), 8.30 (br s, 6H), 11.50 (br s, 6H).

<5-5> Removal of Carbobenzoxy (Cbz) Protecting Group from Terminal Amine Group of the Linker

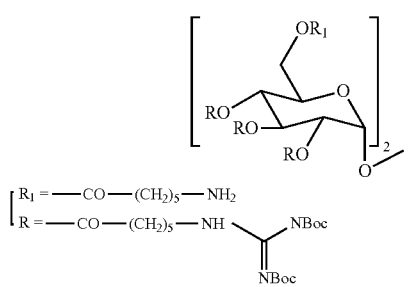

The compound obtained in Example <5-4> (159 mg, 54 mmol) was dissolved in a mixture of methanol and dichloromethane (9:1) (19 ml), Pd/C (10 wt %, 120 mg) was added thereto. The mixture thus obtained was stirred at room temperature under H$_2$ gas (50 psi) for 16 hours, and filtered through celite to remove Pd/C. The filtrate thus obtained was concentrated under a reduced pressure to obtain the title compound as a white sticky solid (130 mg).

$^1$H NMR (MeOD) δ 1.39-1.78 (m, 156H, CH$_3$ and NCH$_2$CH$_2$CH$_2$CH$_2$), 2.25-2.45 (m, 16H, CO—CH$_2$), 2.85-2.99 (m, 4H, CH$_2$NH$_2$), 3.32-3.39 (m, 12H, CH$_2$NH), 3.94-4.11 (m, 2H), 4.09-4.28 (m, 4H), 5.05-5.14 (m, 4H), 5.36 (d, 2H, J=3.6 Hz, anomeric protons), 5.53 (app. t, 2H, J=9.7 Hz).

<5-6> Introduction of Fluorescence Probe (FITC)

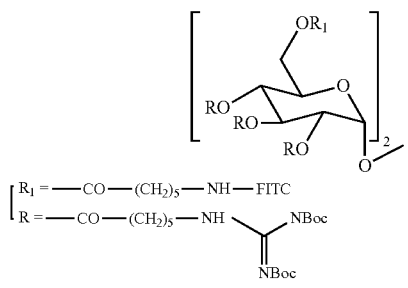

The compound obtained in Example <5-5> (129 mg, 47.83 μmol) was dissolved in a mixture of tetrahydrofuran, ethanol and methanol (6:4:1) (4 ml), fluorescein-5-isocyanate (55 mg, 0.13 mmol) and triethylamine (65 μl, 0.34 mmol) were added thereto, and the mixture thus obtained was stirred at room temperature for one day.

After the completion of the reaction, the reaction mixture was concentrated under a reduced pressure, and then purified by column chromatography (dichloromethane:methanol=10:1) to obtain a dark yellow sticky compound (95 mg).

$^1$H NMR (CDCl$_3$) δ 1.23-1.66 (m, 156H, CH$_3$ and NCH$_2$CH$_2$CH$_2$CH$_2$), 2.11-2.30 (m, 12H, CO—CH$_2$), 3.30-3.48 (m, 12H, CH$_2$NHC=N), 3.51-3.69 (m, 4H, CH$_2$NHC=S), 3.91-4.01 (m, 4H), 4.10-4.20 (m, 2H), 4.92-5.11 (m, 4H), 5.21-5.31 (m, 2H), 5.49 (app. t, 2H, J=9.3 Hz), 6.57-6.79 (m, 10H), 7.10-7.18 (m, 2H), 7.91-8.11 (m, 2H), 8.31-8.49 (m, 4H), 9.04 (br s, 2H), 11.49 (br s, 6H).

<5-7> Removal of N-Boc Protecting Group from N,N'-di-Boc-Guanidine Group

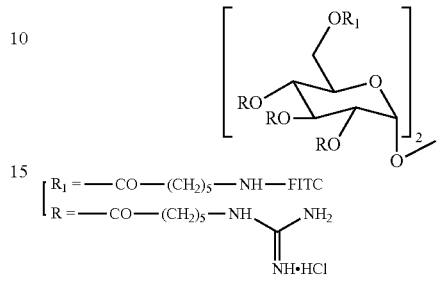

The compound (92 mg, 26.52 μmol) obtained in Example <5-6> was dissolved in HCl gas-saturated ethyl acetate (3.5 ml), and stirred at room temperature for two days.

After the completion of the reaction, the reaction mixture was concentrated under a reduced pressure to remove the solvent, washed with ethyl acetate to remove non-polar impurities, and then purified by MPLC to obtain a yellow sticky compound (42 mg). For analysis, a small amount of the compound was further purified by prep-HPLC (water:acetonitrile=75:25, 220 nm).

$^1$H NMR (MeOD) δ 1.30-1.75 (m, 48H, NCH$_2$CH$_2$CH$_2$CH$_2$), 2.24-2.49 (m, 16H, CO—CH$_2$), 3.11-3.28 (m, 12H, CH$_2$NHC=N), 3.59-3.66 (m, 4H, CH$_2$NHC=S), 4.00-4.09 (m, 2H), 4.10-4.28 (m, 4H), 5.04-5.18 (m, 4H), 5.35 (d, 2H, J=3.4 Hz, anomeric protons), 5.54 (app. t, 2H, J=9.8 Hz), 6.55-6.73 (m, 12H), 7.15-7.18 (m, 2H), 7.73-7.80 (m, 2H), 8.32 (br s, 2H).

Example 6

Preparation of Trehalose Derivative Having Six Guanidine Groups

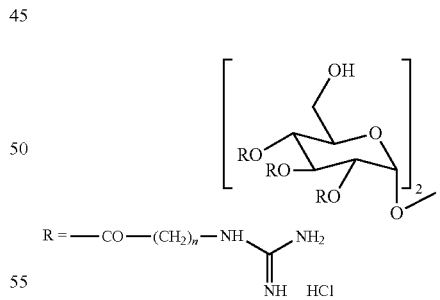

The compound obtained in Example <5-3> (26 mg, 10.59 mmol) was dissolved in HCl gas-saturated ethyl acetate (2 ml), and stirred at room temperature for two days.

After the completion of the reaction, the reaction mixture was concentrated under a reduced pressure to remove the solvent, washed with ethyl acetate to remove non-polar impurities, and then purified by MPLC, to obtain a white sticky compound (13.7 mg). For analysis, a small amount of the compound was further purified by prep-HPLC (water:acetonitrile=75:25, 220 nm).

¹H NMR (D₂O) δ 1.31-1.73 (m, 36H, NCH₂CH₂CH₂CH₂), 2.39-2.62 (m, 12H, CO—CH₂), 3.11-3.28 (m, 12H, NCH₂), 3.81 (app. t, 1H, J=9.12 Hz), 3.95-4.11 (m, 2H), 4.15-4.52 (m, 5H), 4.89-5.12 (m, 2H), 5.19-5.55 (m, 4H).

Example 7

Preparation of Trehalose Derivative Having Eight Guanidine Groups

<7-1> Introduction of Side Chain to Trehalose by Acylation

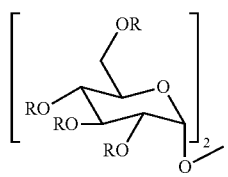

R = —CO—(CH₂)₅—NHBoc

Trehalose hydrate (0.87 g, 2.30 mmol), N-Boc-6-aminohexanoic acid (6.37 g, 27.55 mmol), 1-ethyl-3-(3-dimethylaminopropyl)carbodiimide (5.81 g, 30.30 mmol) and 4-dimethylaminopyridine (0.84 g, 6.89 mmol) were dissolved in N,N-dimethylformamide (24 in) and stirred at room temperature for 48 hours.

After the completion of the reaction, the reaction mixture was subjected to azeotropic distillation along with toluene at 60° C., diluted with ethyl acetate, and the extract was washed several times with saturated aqueous NaHCO₃ and water. The organic layer thus obtained was dried over Na₂SO₄, concentrated under a reduced pressure, and then purified by column chromatography (ethyl acetate:hexane=1:1) to obtain the title compound as a white solid (4.03 g).

¹H NMR (CDCl₃) δ 1.24-1.66 (m, 120H, CH₃ and NCH₂CH₂CH₂CH₂), 2.20-2.37 (m, 16H, CO—CH₂), 3.08-3.21 (m, 16H, NCH₂), 3.83-4.03 (m, 4H), 4.20-4.25 (m, 2H), 4.65-5.00 (m, 7H, NH), 5.01-5.09 (m, 4H), 5.29 (d, 2H, J=3.7 Hz, anomeric protons), 5.48 (app. t, 2H, J=9.7 Hz).

<7-2> Removal of N-Boc Protecting Group from Terminal Amino Group of the Side Chain

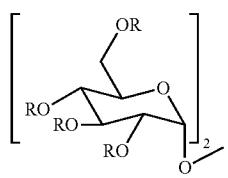

R = —CO—(CH₂)₅—NH₂·TFA

The compound (1.94 g, 0.95 mmol) obtained in Example <7-1> was dissolved in a mixture of trifluoroacetic acid (TFA) and dichloromethane (1:1, 20 ml), and stirred at room temperature for 6 hours.

After the completion of the reaction, the reaction mixture was concentrated under a reduced pressure, and the extract was washed with a mixture of diethylether and methanol (20:1). The product thus obtained was dissolved in water and lyophilized to obtain a brown sticky compound (3.17 g).

¹H NMR (MeOD) δ 1.25-1.39 (m, 16H, NCH₂CH₂CH₂), 1.42-1.66 (m, 32H, NCH₂CH₂CH₂CH₂), 2.10-2.35 (m, 16H, CO—CH₂), 2.71-2.89 (m, 16H, NCH₂), 3.81-3.93 (m, 2H), 4.00-4.15 (m, 4H), 4.91-5.03 (m, 4H), 5.23 (d, 2H, J=3.6 Hz, anomeric protons), 5.35 (app. t, 2H, J=9.7 Hz).

<7-3> Conversion of Amino Group into N,N'-di-Boc-Guanidine Group

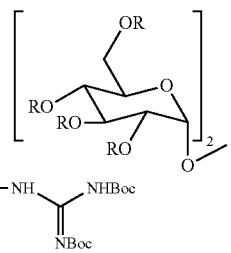

R = —CO—(CH₂)₅—NH—C(=NBoc)—NHBoc

The compound (86 mg, 39.59 μmol) obtained in Example <7-2> was dissolved in a mixture of 1,4-dioxane and water (5:1, 2 ml), triethylamine (0.5 ml, 2.64 mmol), N,N-di-Boc-N'-trifluoromethanesulfonylguanidine (187 mg, 0.48 mmol) were added dropwise thereto, and the mixture was stirred at room temperature for three days.

After the completion of the reaction, the reaction mixture was concentrated under a reduced pressure, diluted with ethyl acetate, and washed with water and saturated aqueous NaCl. The product thus obtained was dried over Na₂SO₄, concentrated under a reduced pressure, and then purified by column chromatography (ethyl acetate:hexane=1:2) to obtain the title compound as a white solid (81 mg).

¹H NMR (CDCl₃) δ 1.28-1.71 (m, 192H, CH₃ and NCH₂CH₂CH₂CH₂), 2.20-2.39 (m, 16H, CO—CH₂), 3.33-3.46 (m, 16H, NCH₂), 3.94-4.01 (m, 4H), 4.16-4.24 (m, 2H), 4.97-5.10 (m, 4H), 5.27 (d, 2H, J=3.7 Hz, anomeric protons), 5.45 (app. t, 2H, J=9.7 Hz), 8.31 (br s, 8H), 11.50 (br s, 8H).

<7-4> Conversion of Amino Group into N,N'-di-Boc-Guanidine Group

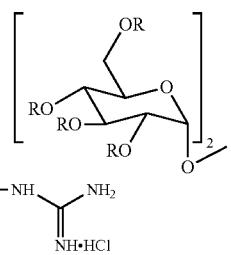

R = —CO—(CH₂)₅—NH—C(=NH·HCl)—NH₂

The compound obtained in Example <7-3> (20 mg, 6.28 μmol) was dissolved in HCl gas-saturated ethyl acetate (3 ml), and stirred at room temperature for two days.

After the completion of the reaction, the reaction mixture was concentrated under a reduced pressure to remove the solvent, washed with ethyl acetate to remove non-polar impurities, and then purified by MPLC to obtain a white sticky compound (13.7 mg). For analysis, a small amount of the compound was further purified by prep-HPLC (water:acetonitrile=75:25, 220 nm).

¹H NMR (D₂O) δ 1.29-1.73 (m, 48H, NCH₂CH₂CH₂CH₂), 2.31-2.49 (m, 16H, CO—CH₂), 3.12-3.22 (m, 16H, NCH₂), 4.02-4.13 (m, 2H), 4.21-4.40 (m, 4H), 5.15-5.27 (m, 4H), 5.45 (d, 2H, J=3.5 Hz, anomeric protons), 5.58 (app. t, 2H, J=9.7 Hz).

Example 8

Preparation of Glucose Derivative Having Eight Guanidine Groups

<8-1> Introduction of Side Chain to Glucose by Acylation

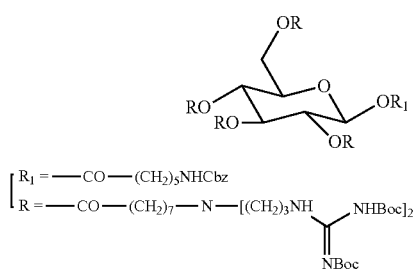

The compound obtained in Preparative Example <5-5> (50 mg, 0.125 mmol), a branched linker having two guanidine groups (757 mg, 1.000 mmol), 1-ethyl-3-(3-dimethylaminopropyl)carbodiimide (192 mg, 1.000 mmol) and 4-dimethylaminopyridine (23 mg, 0.188 mmol) were dissolved in N,N-dimethylformamide (2 ml) and stirred at room temperature for three days.

After the completion of the reaction, the reaction mixture was washed several times with water and aqueous $NaHCO_3$. The organic layer thus obtained was dried over $Na_2SO_4$, concentrated under a reduced pressure, and then purified by column chromatography (dichloromethane:methanol=10:1) to obtain the title compound as a sticky solid (306 mg).

$^1$H NMR ($CDCl_3$): δ 1.27-1.75 (m, 206H), 2.04-2.53 (m, 32H), 3.15-3.18 (m, 2H), 3.46 (brs, 16H), 3.64-3.81 (m, 2H), 4.16 (brs, 2H), 4.46 (d, J=7.8 Hz, 1H), 4.94-5.24 (m, 5H), 7.34 (s, 5H), 8.52 (s, 8H), 11.49 (s, 8H).

<8-2> Removal of Carbobenzoxy (Cbz) Protecting Group from Terminal Amine Group of the Linker

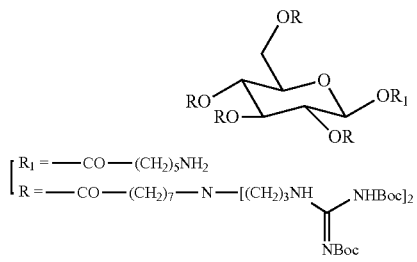

The compound obtained in Example <8-1> (105 mg, 0.028 mmol) was dissolved in ethanol (8 ml), Pd/C (10 wt %, 100 mg) was added thereto. This mixture thus obtained was stirred at room temperature under $H_2$ gas (1 atm) for one day, and filtered through celite to remove Pd/C. The filtrate thus obtained was concentrated under a reduced pressure to obtain the title compound as a white sticky solid (78 mg).

$^1$H NMR ($CDCl_3$): δ 1.25-1.86 (m, 206H), 2.18-2.26 (m, 32H), 3.15-3.18 (m, 2H), 3.46 (brs, 18H), 3.63-4.16 (m, 6H), 4.11-4.16 (m, 3H), 4.52 (brs, 1H), 4.94-5.09 (m, 2H), 5.21 (t, J=9.0 Hz, 1H), 8.60 (s, 8H), 11.41 (s, 8H).

<8-3> Introduction of Fluorescence Probe (FITC)

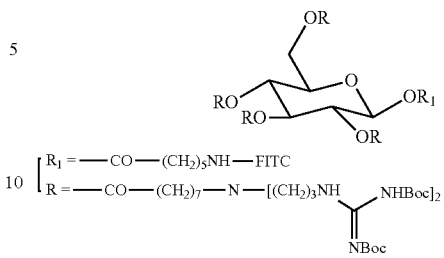

The compound obtained in Example <8-2> (75 mg, 0.020 mmol) was dissolved in a mixture of tetrahydrofuran and ethanol (5:2) (3.5 ml), fluorescein-5-isocyanate (10 mg, 0.024 mmol) and triethylamine (24 μl, 0.163 mmol) were added thereto, and the mixture was stirred at room temperature for one day.

After the completion of the reaction, the reaction mixture was concentrated under a reduced pressure, and then purified by column chromatography (dichloromethane:methanol=8:1) to obtain a dark yellow sticky compound (29 mg).

$^1$H NMR ($CDCl_3$): δ 1.18-1.61 (m, 206H), 2.15-2.95 (m, 34H), 3.39 (brs, 18H), 3.56-3.80 (m, 6H), 4.00-4.16 (m, 3H), 4.43 (brs, 1H), 4.81-5.27 (m, 3H), 6.42-6.99 (m, 6H), 7.27 (brs, 1H), 7.74-7.78 (m, 1H), 7.89 (s, 1H), 8.43 (s, 8H), 11.37 (s, 8H).

<8-4> Removal of N-Boc Protecting Group from N,N'-di-Boc-Guanidine Group

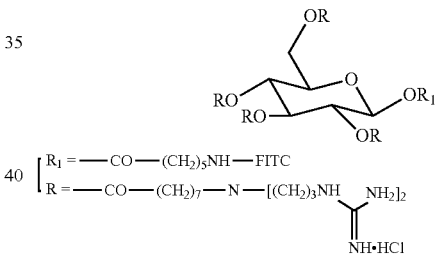

The compound obtained in Example <8-3> (29 mg) was dissolved in ethyl acetate (1 ml), HCl gas-saturated ethyl acetate (3 ml) was added dropwise thereto, and the mixture was stirred at room temperature for one day.

After the completion of the reaction, the reaction mixture was concentrated under a reduced pressure to remove the solvent, washed with ethyl acetate to remove non-polar impurities, and then purified by MPLC chromatography (0.1% trifluoroacetic acid-containing water:acetonitrile=1:1-1:2) to obtain a light green compound (3.5 mg).

$^1$H NMR ($CD_3OD$): δ 1.36-1.71 (m, 62H), 2.01-2.42 (m, 34H), 3.29-3.42 (m, 18H), 3.52-3.89 (m, 6H), 4.11-4.30 (m, 3H), 4.59-4.71 (m, 1H), 4.81-5.26 (m, 3H), 6.52-6.68 (m, 6H), 7.15 (d, J=8.3 Hz, 1H), 7.67 (d, J=7.1 Hz, 1H), 8.37 (s, 1H).

Test Example 1

Measurement of Permeation into Mouse Brain and Distribution Therein

The compounds obtained in Example 1 (94.5 mg/kg), Example 2 (59.5 mg/kg), Example 3 (84.5 mg/kg), Example 5 (90.9 mg/kg) and Example 8 (83.1 mg/kg) were each dissolved in distilled water, and intraperitoneally injected into eight-week old C57BL/6 mice (available from Hyochang Science Inc., Korea). After 20 min, the injected mice were treated with a solution (4% para-formaldehyde in PBS (pH 7.4)), the brain of each mouse was collected and stored in a 0.5 M sucrose PBS solution for one day.

In a cryostat, the brain was sliced into 15 μm thick slices, and each slice was placed on a slide glass, dried at 37° C., washed with PBS, treated with 0.3% triton X-100 at room temperature for 15 min, and then observed with a confocal microscope. The results are shown in FIG. 1.

In FIG. 1, (A) shows the result obtained for the mice injected with only distilled water as a control, (B) to (F) show the results obtained from the mice injected with the compound of Examples 1 to 5, respectively.

As shown in FIG. 1, the inositol, the trehalose and the monosaccharide derivatives prepared according to the present invention readily pass through the blood-brain barrier to permeate into the brain tissue.

As described above, in accordance with the present invention, the inositol and the trehalose derivatives have high BBB permeability and can easily be delivered to the brain tissues, and thus can be effectively used for the treatment of neurodegenerative diseases such as Alzheimer's disease, Huntington's disease, and other related diseases.

While the invention has been described with respect to the above specific embodiments, it should be recognized that various modifications and changes may be made to the invention by those skilled in the art, which also fall within the scope of the invention as defined by the appended claims.

What is claimed are:

1. A trehalose compound of Formula (3) or a salt thereof:

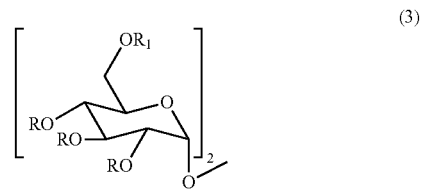

wherein,
R is

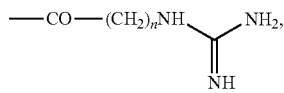

n being an integer in the range of 1 to 12; and
$R_1$ is hydrogen, R, alkyl or —COR', R' being hydrogen, alkyl, aminoalkyl, arylalkyl, cycloalkyl, heteroalkyl or a phosphor.

2. A pharmaceutical composition containing the compound according to claim 1 or a salt thereof as an active ingredient.

3. A method for treating a Huntington's disease, comprising administering the pharmaceutical composition of claim 2 to a subject in need thereof.

* * * * *